(12) United States Patent
Melanson et al.

(10) Patent No.: US 10,451,622 B2
(45) Date of Patent: Oct. 22, 2019

(54) CENTRIPETAL MICROFLUIDIC PLATFORM FOR LAL REACTIVE SUBSTANCES TESTING

(71) Applicant: General Electric Company, Schenectady, NY (US)

(72) Inventors: Paul Charles Melanson, Boulder, CO (US); Richard Douglas Godec, Boulder, CO (US); Matthew Kaddeland Stonesmith, Boulder, CO (US); Darren Barry Smith, Boulder, CO (US); Chao Sun, Shanghai (CN)

(73) Assignee: BL TECHNOLOGIES, INC., Minnetonka, MN (US)

( * ) Notice: Subject to any disclaimer, the term of this patent is extended or adjusted under 35 U.S.C. 154(b) by 0 days.

(21) Appl. No.: 16/133,666

(22) Filed: Sep. 17, 2018

(65) Prior Publication Data

US 2019/0018013 A1    Jan. 17, 2019

Related U.S. Application Data

(62) Division of application No. 14/434,312, filed as application No. PCT/US2013/063639 on Oct. 7, 2013, now Pat. No. 10,082,505.

(Continued)

(51) Int. Cl.
*B01L 3/00* (2006.01)
*G01N 33/569* (2006.01)
(Continued)

(52) U.S. Cl.
CPC ...... *G01N 33/56911* (2013.01); *B01L 3/5027* (2013.01); *B01L 3/5085* (2013.01);
(Continued)

(58) Field of Classification Search
None
See application file for complete search history.

(56) References Cited

U.S. PATENT DOCUMENTS

| 3,971,186 A | 7/1976 | Havelka |
| 4,370,413 A | 1/1983 | Neeman |

(Continued)

FOREIGN PATENT DOCUMENTS

| CA | 2156226 | 2/1996 |
| CA | 2420682 | 3/2002 |

(Continued)

OTHER PUBLICATIONS

Notification of Reasons for Refusal in connection with related Japanese Patent Application No. 2015-535861 dated Feb. 27, 2018.

(Continued)

*Primary Examiner* — Rebecca L Martinez
(74) *Attorney, Agent, or Firm* — Webman, Hessler

(57) ABSTRACT

A centripetal microfluidic platform comprised of a microfluidics disc and a reader for testing LAL-reactive substances in fluid samples is provided. The microfluidic disc may comprise at least two testing areas wherein each testing area includes a reservoir portion for receiving at least one fluid sample. The disc may comprise a distribution network portion in fluid communication with the reservoir portion. Each distribution network portion may comprise a distribution network of at least four (4) channels, wherein each channel has a metering portion and at least one analysis chamber portion. The analysis chamber portion may comprise a mixing chamber for mixing samples and reagents and an optical chamber portion that is compatible with an optical reader. The metering portion may be sized to meter an aliquot of the fluid sample for analysis in the analysis chamber portion. At least one analysis chamber portion has at least one reagent isolated therein. The centripetal micro- (Continued)

fluidic platform further includes a reader for testing fluid samples within a microfluidic disc comprising an enclosure, an optical bench, a centripetal disc drive, and a controller. A method for testing at least one fluid sample for LAL-reactive substances is also provided.

10 Claims, 12 Drawing Sheets

Related U.S. Application Data

(60) Provisional application No. 61/710,898, filed on Oct. 8, 2012, provisional application No. 61/710,908, filed on Oct. 8, 2012, provisional application No. 61/710,903, filed on Oct. 8, 2012, provisional application No. 61/710,990, filed on Oct. 8, 2012.

(51) Int. Cl.
 *G01N 33/579* (2006.01)
 *G01N 21/17* (2006.01)

(52) U.S. Cl.
 CPC ........ *B01L 3/502715* (2013.01); *G01N 21/17* (2013.01); *G01N 33/579* (2013.01); *B01L 2200/0605* (2013.01); *B01L 2200/0684* (2013.01); *B01L 2300/021* (2013.01); *B01L 2300/087* (2013.01); *B01L 2300/0816* (2013.01); *B01L 2300/0829* (2013.01); *B01L 2300/0861* (2013.01); *B01L 2300/0864* (2013.01); *B01L 2300/0867* (2013.01); *B01L 2300/16* (2013.01); *B01L 2400/0406* (2013.01); *B01L 2400/0409* (2013.01); *B01L 2400/049* (2013.01); *B01L 2400/0487* (2013.01); *B01L 2400/0622* (2013.01); *B01L 2400/0688* (2013.01); *B01L 2400/0694* (2013.01); *G01N 2400/10* (2013.01); *G01N 2400/50* (2013.01); *Y10T 436/2575* (2015.01)

(56) References Cited

U.S. PATENT DOCUMENTS

| | | | |
|---|---|---|---|
| 4,717,658 A | 1/1988 | Michaels | |
| 4,819,713 A | 4/1989 | Weisman | |
| 4,824,303 A | 4/1989 | Dinger | |
| 4,879,634 A | 11/1989 | Storrow | |
| 4,909,752 A | 3/1990 | Hallum | |
| 5,010,444 A | 4/1991 | Storrow | |
| 5,071,013 A | 12/1991 | Peterson | |
| 5,220,485 A | 6/1993 | Chakrabarti | |
| 5,224,016 A | 6/1993 | Weisman | |
| 5,550,030 A | 8/1996 | Tanaka | |
| 5,571,683 A | 11/1996 | Nakajima | |
| 5,726,404 A | 3/1998 | Brody | |
| 5,859,764 A | 1/1999 | Davis | |
| 6,212,075 B1 | 4/2001 | Habing | |
| 6,270,982 B1 | 8/2001 | Jordan | |
| 6,285,564 B1 | 9/2001 | O'Brien | |
| 6,306,577 B1 | 10/2001 | Tamura | |
| 6,319,469 B1 | 11/2001 | Mian | |
| 6,687,130 B2 | 2/2004 | Adams | |
| 6,887,130 B2 | 5/2005 | Lee | |
| 6,900,019 B1 | 5/2005 | Horton | |
| 7,031,167 B1 | 4/2006 | Zagoory | |
| 7,180,737 B2 | 2/2007 | Straub, Jr. | |
| 7,322,843 B1 | 1/2008 | Lee | |
| 7,349,221 B2 | 3/2008 | Yurko | |
| 7,807,448 B2 | 10/2010 | Glezer | |
| 8,045,332 B2 | 10/2011 | Lee | |
| 2002/0027133 A1 | 3/2002 | Kellogg | |
| 2002/0137218 A1 | 9/2002 | Mian | |
| 2002/0185183 A1 | 12/2002 | O'Connor | |
| 2004/0121450 A1 | 6/2004 | Pugia | |
| 2004/0131450 A1 | 7/2004 | Yang | |
| 2004/0229349 A1 | 11/2004 | Daridon | |
| 2005/0026239 A1 | 2/2005 | Castro | |
| 2005/0048655 A1 | 3/2005 | Novitsky | |
| 2005/0106066 A1 | 5/2005 | Saltsman | |
| 2005/0170515 A1* | 8/2005 | Moore | B01L 3/502715 436/45 |
| 2007/0231217 A1 | 10/2007 | Clinton | |
| 2007/0253169 A1 | 11/2007 | Clawser | |
| 2008/0187445 A1 | 8/2008 | Gale | |
| 2008/0190220 A1 | 8/2008 | Backes | |
| 2008/0239690 A1 | 10/2008 | Harvey | |
| 2009/0139578 A1 | 6/2009 | Kim | |
| 2009/0238724 A1 | 9/2009 | Yamamoto | |
| 2009/0311796 A1 | 12/2009 | Griss | |
| 2010/0330597 A1 | 12/2010 | Tsuchiya | |
| 2011/0079094 A1 | 4/2011 | Gransee | |
| 2011/0124132 A1 | 5/2011 | Kim | |
| 2011/0143364 A1 | 6/2011 | Kim | |
| 2011/0201049 A1* | 8/2011 | Wainwright | G01N 33/579 435/34 |
| 2011/0261537 A1 | 10/2011 | Sporer | |
| 2012/0244607 A1 | 9/2012 | Iwamoto | |
| 2015/0060272 A1 | 3/2015 | Blidner | |
| 2015/0233917 A1 | 8/2015 | Melanson | |
| 2015/0260719 A1 | 9/2015 | Godec | |
| 2015/0293097 A1 | 10/2015 | Godec | |

FOREIGN PATENT DOCUMENTS

| | | |
|---|---|---|
| CA | 2820483 | 7/2007 |
| CA | 2732011 | 2/2010 |
| CA | 2755276 | 9/2010 |
| CN | 1208464 | 2/1999 |
| CN | 101368967 | 2/2009 |
| CN | 101387647 | 3/2009 |
| CN | 101389960 | 3/2009 |
| CN | 101529246 | 9/2009 |
| CN | 102177439 | 9/2011 |
| CN | 102441356 | 5/2012 |
| EP | 0320154 | 6/1989 |
| EP | 0649021 | 4/1995 |
| EP | 0690308 | 1/1996 |
| EP | 0921397 | 6/1999 |
| EP | 0957366 | 11/1999 |
| EP | 1955770 | 8/2008 |
| EP | 1983347 | 10/2008 |
| JP | 6193958 | 5/1986 |
| JP | H03220456 A | 9/1991 |
| JP | 10253630 | 9/1998 |
| JP | 2001503854 | 3/2001 |
| JP | 2003533681 | 11/2003 |
| JP | 2004212120 | 7/2004 |
| JP | 2005519304 | 6/2005 |
| JP | 2005524058 | 8/2005 |
| JP | 2007501020 | 1/2007 |
| JP | 2009521686 | 6/2009 |
| JP | 2010042020 | 2/2010 |
| JP | 2012132879 | 7/2012 |
| WO | 9721090 | 6/1997 |
| WO | 9943432 A1 | 9/1999 |
| WO | 0187486 | 11/2001 |
| WO | 2004065930 | 8/2004 |
| WO | 2006009724 | 1/2006 |
| WO | 2006069757 | 7/2006 |
| WO | 2006070376 | 7/2006 |
| WO | 2007052648 | 5/2007 |
| WO | 2008139544 | 11/2008 |
| WO | 2009005231 | 1/2009 |
| WO | 2009105711 | 8/2009 |
| WO | 2011096782 | 8/2011 |

OTHER PUBLICATIONS

Notification of Reasons for Refusal in connection with related Japanese Patent Application No. 2015-535862 dated Feb. 27, 2018.

(56) References Cited

OTHER PUBLICATIONS

U.S. Non-final Office Action dated Aug. 29, 2016 for related U.S. Appl. No. 14/434,364, filed Apr. 8, 2015.
U.S. Non-final Office Action dated Jan. 9, 2018 for related U.S. Appl. No. 15/719,464, filed Sep. 28, 2017.
Chang et al., "Feasibility of on-chip detection of endotoxin by LAL test", Biotechnology and bioprocess engineering, pp. 132-136, Jan. 1, 2004.
International Invitation to Pay Additional Fees issued in connection with corresponding PCT Application No. PCT/US2013/063649 dated Feb. 17, 2014.
International Search Report and Written Opinion issued in connection with corresponding PCT Application No. PCT/US2013/038638 dated Jan. 7, 2014.
Notification to Grant Patent Right for Invention for corresponding Chinese Application No. 201380052528.7 dated Jan. 22, 2017.
Office Action dated Sep. 8, 2017 for related U.S. Appl. No. 14/434,312.
Notification of Reasons for Refusal issued in connection with corresponding JP Application No. 2015-535859 dated Jul. 18, 2017.
Notification of Reasons for Refusal issued in connection with related JP Application No. 2015-535855 dated Jul. 18, 2017.
Fourth Office Action and Search issued in connection with corresponding CN Application No. 201380052524.9 dated Jul. 31, 2017.
Japanese Search Report issued in connection with related JP Application No. 2015-535862 dated Jun. 21, 2017.
Japanese Search Report issued in connection with related JP Application No. 2015-535861 dated Jun. 21, 2017.
U.S. Non-Final Office Action issued in connection with related U.S. Appl. No. 14/434,361 dated Oct. 26, 2016.
Nichols et al., "LALreview", PryoSense®-PAT for WFI, Published by Lonza, Issue No. 1, pp. 1-6, 2008.
WinKQCL®4., "Endotoxin Detection and Analysis Sollware", Lonza, Copyright, pp. 1-11, Mar. 2009.
Unofficial English Translation of Chinese Office Action issued in connection with related CN Application No. 201380052528.7 dated Jul. 12, 2016.
Unofficial English Translation of Chinese Office Action issued in connection with related CN Application No. 201380052524.9 dated Dec. 4, 2015.
Unofficial English Translation of Chinese Office Action issued in connection with related CN Application No. 201380052528.7 dated Oct. 27, 2015.
Hemker et al., "The Kinetics of Enzyme Cascade Systems General Kinetics of Enzyme Cascades", The Procedures of the Royal Society, B (Biological Sciences), vol. No. 173, pp. 411-420,1969.
Bryant et al., "Endotoxin Contamination of Enzyme Conjugates Used in Enzyme-Linked Immunosorbent Assays", Journal of Clinical Microbiology, vol. No. 17, Issue No. 6, pp. 1050-1053, Jun. 1983.
Baines, "Endotoxin Testing", In: Handbook of Microbiological Quality Control in Pharmaceuticals and Medical Devices, pp. 144-167, 2003.
Suh et al., "Feasibility of On-Chip Detection of Endotoxin by LAL Test", Biotechnology and Bioprocess Engineering, vol. No. 9, pp. 132-136.01 Jan. 2004.
Gee et al., "A Multi-Center Comparison Study Between ne Endosafe PTS(TM) Rapid Release Testing System and 5 Traditional Test Methods for Detecting Endotoxin in Cell Theraphy Products", Cytotherapy, vol. No. 10, Issue No. D 4, pp. 427-435, Aug. 22, 2008.
Mitsumoto et al., Novel Endotoxin Assay by Laser Light-Scattering Particle-Counting Method, Journal of Clinical I, D1 1 Laboratory AnalysiS, vol. No. 23, Issue No. 2, pp. 117-124, Jan. 1, 2009.
Cooper et al., "Automated Endotoxin Testing Program for High-Risk Level Compounded Sterile Preparations at an Institutional Compounding Pharmacy", American Journal of Health-System Pharmacy, AJHP: Official Journal of the American Society of Health=System Pharmacists, vol. No. 67, Issue No. 4, pp. 280-286, Feb. 15, 2010.

Lonza, "Endoxtoxin Detection", Products and Services, pp. 1-36, May 1, 2010.
The United States Pharmacopeia, "Bacterial Endotoxins Test", Biological Tests and Assays, USP Chapter 85, Reissue, pp. R65-R69, Oct. 1, 2010.
European Pharmacopoeia, "2.6.14 Bacterial Endotoxins", Seventh Edition, vol. No. 1, pp. 171-175, 2010.
Tsougeni et ai., "Smart" Polymeric Microfluidics Fabricated by Plasma Processing: Controlled Wetting. Capillary Filling and Hydrophobic Valving, The Royal Society of Chemistry, vol. No. 10, pp. 462-469, Nov. 30, 2009.
"Limulus Amebocyte Lysate (LALI) Kinetic-QCL(TM)", Lonza, pp. 1-19, Jan. 1, 2011.
American National Standard, "Bacterial Endotoxins—Test Methods, Routine Monitoring, and Alternatives to Batch Testing", ANSi/AAMI ST72:2011, pp. 1-34, 2011.
The Japanese Pharmacopeia, "4.01 Bacterial Endotoxin Test", Sixteenth Edition, pp. 92-96, 2011.
Harwood. "3-Dimensional Compact Disc (CD) Microfluidic Platform", A Thesis, pp. 1-78, 2011.
ICH Harmonised Tripartite Guideline, "Evaluation and Recommendation of Pharmacopoeial Texts for Use in be ICH Regions on Bacterial Endotoxins Test General Chapter", Q4B ANNEX 14, Step 4 version, Oct. 18, 2012.
The United States Pharmacopeia, "Transfusion and Infusion Assemblies and Similar Medical Devices", USP Chapter 161, vol. No. 1, pp. 131-131, May 1, 2013.
PCT Search Report and Written Opinion issued in connection with corresponding Application No. PCT/US2013/063625 dated Jan. 24, 2014.
International Search Report and Written Opinion issued in connection with corresponding PCT Application No. PCT/US2013/063645 dated Feb. 17, 2014.
PCT Search Report and Written Opinion issued in connection with corresponding Application No. PCT/US2013/063649 dated Apr. 30, 2014.
PCT Search Report and Written Opinion issued in connection with related Application No. PCT/US2013/63639 dated Jun. 25, 2014.
Notice of Allowance dated May 17, 2018 for U.S. Appl. No. 14/434,312 (pp. 1-8).
Dungan et al., (Aerobiologia. 2009.25:265-273.
Stanson (2008. Endotoxin Testing by Kinetic-QCL Method. SOP#: CPL-0243. Version :1, Effective Date Apr. 30, 2008. University of Pittsburg Cancer Institute Immunologic Monitoring and Cellular Products Laboratory).
Office Action dated May 16, 2018 for related U.S. Appl. No. 15/884,347 (pp. 1-12).
Notice of Allowability dated Jul. 6, 2018 for U.S. Appl. No. 14/434,312 (pp. 1-3).
Office Action dated Aug. 13, 2018 for U.S. Appl. No. 15/719,464 (pp. 1-14).
This application is related to Paul Charles Melanson et al., filed Apr. 8, 2015, U.S. Appl. No. 14/434,312.
This application is related to Richard Douglas Godec et al., filed Apr. 8, 2015, U.S. Appl. No. 14/434,361.
This application is related to Richard Douglas Godec et al., filed Apr. 8, 2015, U.S. Appl. No. 14/434,273.
This application is related to Paul Charles Melanson et al., filed Apr. 8, 2015, U.S. Appl. No. 14/434,364.
This application is related to Richard Douglas Godec et al., filed Sep. 28, 2017, U.S. Appl. No. 15/719,464.
Notice of Allowance dated Jan. 23, 2019 for U.S. Appl. No. 15/884,347 (pp. 1-8).
First Examination Report dated Jan. 31, 2019 in Indian Patent Application No. 2285/CHENP/2015.
First Examination Report dated Jan. 15, 2019 in Indian Patent Application No. 2155/CHENP/2015.
Examination Report dated Oct. 25, 2018 in EP Patent Application No. 17192314.7.

* cited by examiner

CENTRIPETAL MICROFLUIDIC PLATFORM FOR LAL REACTIVE SUBSTANCES TESTING

CROSS-REFERENCE TO RELATED APPLICATIONS

This application is a divisional of U.S. patent application Ser. No. 14/434,312 filed Apr. 8, 2015, which is a national stage application under 35 U.S.C. Section 371(c) of PCT application serial number PCT/US2013/063639, filed Oct. 7, 2013, which claims priority to Provisional Patent Application Ser. No. 61/710,908 filed Oct. 8, 2012 and titled MICROFLUIDIC BACTERIA ENDOTOXIN TESTING METHOD AND APPARATUS; Provisional Patent Application Ser. No. 61/710,990 filed Oct. 8, 2012 and titled CENTRIPETAL MICROFLUIDIC PLATFORM FOR BACTERIAL ENDOTOXIN TESTING; Provisional Patent Application Ser. No. 61/710,898 filed Oct. 8, 2012 and titled SENSITIVE AND RAPID METHOD FOR DETECTION OF LOW LEVELS OF ENDOTOXINS USING LAL REAGENTS; and Provisional Patent Application Ser. No. 61/710,903 filed Oct. 8, 2012 and titled MICROPLATES PRELOADED WITH ENDOTOXIN DETECTION REAGENTS WITH CALIBRATION MEANS; all of the above listed applications are incorporated herein by reference.

FIELD OF INVENTION

Embodiments of the present invention direct to the field of determining the concentration of LAL-reactive substances in a fluid sample, and more particularly, embodiments of the present invention relate to a centripetal microfluidic platform and disc for measuring the concentration of LAL-reactive substances in fluid samples.

BACKGROUND OF THE INVENTION

Microbial contamination, such as Gram positive bacteria, Gram negative bacteria, yeast, and fungi may cause severe illness and even death in humans. When people become infected with gram negative bacteria, the bacteria may produce fever-inducing bacterial endotoxins. Endotoxins can be dangerous and even deadly to humans. Endotoxin molecules, which are lipopolysaccharide components of cell walls of gram negative bacteria, can be present in drug formulations and surfaces of medical devices, independent of microbial contamination. Endotoxin contamination can happen even if a system passes a sterility test, which is why an independent endotoxin test is required.

Currently, a variety of tests have been developed to detect the presence of endotoxin in or on the sample being tested using hemocyte lysates from horseshoe crabs. Clotting will occur when the hemocyte lysate is exposed to the endotoxin. Hemocyte lysate is amebocyte lysate produced from the hemolymph of various horseshoe crab species, including the *Limulus, Tachypleus*, and *Carcinoscorpius* species. A commonly used amebocyte lysate is produced from the hemolymph of *Limulus*, or *Tachypleus* species, is referred to as *Limulus* amebocyte lysate ("LAL"). Routine tests that use LAL as a test reagent include gel clot assays, end point turbidimetric assays, kinetic turbidimetric assays, endpoint chromogenic assays, and kinetical chromogenic assays. Tests that use LAL reagent may also be used to test for certain types of glucans, a marker for fungal contamination.

More information on LAL assays and the standards used may be found in United States Pharmacopeia ("USP") Chapter 85 "Bacterial Endotoxins Test" ("BET"), Japanese Pharmacopeia 4.01 "Bacterial Endotoxin Test", European Pharmacopoeia 2.6.14 "Bacterial Endotoxins", and other equivalent national Pharmacopeias. Additional internationally harmonized pharmacopeia information can be found in ICH Q4B Annex 14 "Bacterial Endotoxin Test General Chapter". For endotoxin testing in medical devices, information can be found in USP Chapter 161 "Transfusion and Infusion Assemblies and Similar Medical Devices" and ANSI/AAMI ST72 "Bacterial endotoxins—Test methods, routine monitoring, and alternatives to batch testing". These standards and procedures may be generally referred to as compendia.

Manufacturers in the pharmaceutical, medical device and food industries must meet certain standards to make sure their products do not contain microbial or endotoxin contamination. These industries require frequent, accurate, and sensitive testing for the existence of endotoxins to meet various safety standards, such as those set by the United States Food and Drug Administration, or the Environmental Protection Agency. These agencies accept many of the compendia procedures standards. Thus, if manufacturers want to obtain government approval to release a new product to market, many of the FDA requirements may be met if the products comply with the methods and standards in the compendia listed above. This can substantially reduce the cost to manufacturers to obtain FDA approval of new products.

These agencies also have strict reporting requirements when test results show bad results, or endotoxin concentrations outside the expected range. Such non-compliant results must be thoroughly investigated to find the root cause and explained to the regulating agency. This is time consuming and costly. If manufacturers can show the non-compliant result occurs because of an anomaly in the test itself, and not because of the presence of an endotoxin actually in or on the sample, many of the reporting requirements to the agencies may be satisfied. This may reduce the time and cost incurred to fulfill such reporting obligations. To date, there are no known methods or apparatuses that are capable of distinguishing between anomalies or errors in the test itself and an anomaly in the sample.

These assays in the various compendia require aqueous solutions comprising known concentrations of an endotoxin for use as "standards". These aqueous solutions are typically unstable; therefore they are usually made from powdered toxins at the test location just prior to testing. The LAL reagent also usually comes in powder form and must be reconstituted in an aqueous solution before use.

Preparation of the endotoxin and LAL powders is difficult due to the slow solvation of the critical biological molecules and their propensity to stick to surfaces during mixing and condense on surfaces afterwards. The LAL reagent also starts reacting slowly upon reconstitution and has a very short shelf life. While the best practice would be to mix these immediately before use, workflow typically dictates mixing them at the start of the process. Also, the process of preparation is prone to contamination from endotoxins which are ubiquitous in the environment.

The agencies also require a series of calibration tests to ensure the equipment and reagents used are functioning properly. The calibration tests and sample measurements must also be made more than once. The current laboratory method of complying with BET and other compendia is very detailed and requires repetitive and highly precise measuring of fluid volumes for distribution into multiple inlets of a microplate or the like without contamination.

The most common method of performing an LAL analysis is with a microwell plate and reader. A matrix of reaction wells, open at the top and with a clear window on the bottom, are placed in a heated spectrophotometric reader used for multiple, simultaneous assays. There are many drawbacks, including the lengthy time it takes to prepare the plate, its high cost, the opportunity for mistakes and contamination, and the need to have the work done by a technician specifically trained for and dedicated to this task.

Highly skilled operators are continuously monitored to ensure proper technique and accuracy of measurement and testing, and the operators are retrained as needed so as to ensure accuracy of the repetitive actions. Typical methods may have as many as 248 slow and time consuming pipetting steps, making it an error prone method due to its complexity and contamination prone due to its length and number of manipulations.

Methods and devices have been developed to reduce the amount of steps or automated some or all of the steps in endotoxin testing. Some methods include automating one or more pipetting or aliquoting steps, automated mixing of samples, or preloading reagents in test substrates that allow only a very limited number of tests. All of the developed methods or devices, however, are missing one or more of the following aspects, low cost automation designed into the substrate, disposable clean substrate to insure cleanliness, compendial testing compliance on each substrate, built in individual test measurement validation, and simplicity of measurement operation.

Other microfluidic methods exist to partially automate the assay process, but these are not fully compatible with the compendia methods due to their limited size and their reliance on a stored calibration rather than on calibrations run at the same time in the same apparatus using the same reagents and standards. It also requires a precise sample measurement; no aliquots are generated by the instrument or apparatus itself.

Other automated methods rely on robotics to measure and distribute samples and reagents in a microplate. Once prepared, the plate is loaded in a reader, either manually or using another robot. The robot is typically a pipette-based dispensing system which accurately transfers samples and reagents from a vial rack to the plate, replacing pipette tips to prevent cross-contamination. This is an expensive system which needs frequent validation of its robotic operations and multiple disposables (pipette tips, multiwell plates, dilution tubes, pipette filling trays, sampling vials, etc.) for each run. It also prepares the wells in sequence, and like manual preparation, cannot start all the reactions simultaneously. Contamination is still an issue and since the process is typically unmonitored, there is no legitimate way of rejecting contaminated samples for cause.

An automated system based on flow injection or sequential injection analysis has also been developed. It a significant improvement in that it does analyses simultaneously and thus faster and as specified by compendia, and uses disposable microfluidics which do not require cleaning and are not prone to contamination.

To date, however, there are no known methods or apparatuses that are capable of reducing the number steps the user has to perform in preparing and measuring both the calibration standards and measurement samples while complying with compendia.

Accordingly, there exists a need for a more semi-automated testing method or procedure for testing and analyzing the endotoxin concentration in a fluid sample which reduces or eliminates the amount of potential operator error and also complies with compendia.

BRIEF SUMMARY OF THE INVENTION

The present invention includes a microfluidic disc, systems and methods capable of performing LAL analysis, including multiple analyses for a single sample from a single source, analyses from the same source that have been "spiked" with additional endotoxin or glucan, standard concentrations of endotoxin or glucan, and blank water ("blank" or "LAL reagent water"). These analyses can be performed simultaneously in the same microfluidic disc that may be a disposable device.

The present invention may be used to detect any LAL-reactive substance. As used herein LAL-reactive substance means a substance that reacts with an LAL reagent (detection reagent), including endotoxin or 1,3-.beta.-D-glucans such as laminarin and curdlan. The present invention may also be used with any commercial source of LAL reagent or detection reagent, or any other reagents suitable for assaying LAL-reactive substances.

The present invention may reduce the number of steps the user has to perform in preparing and measuring both the calibration standards and samples. It may reduce the need for a high level of skill, experience, and training, and reduces costs, times, and the opportunity for human error. The present invention may also be utilized to distinguish between anomalies or errors in the test itself and an anomaly in the sample. In addition, embodiments of the invention may be utilized in a manner that complies with compendia requirements and FDA regulations.

Embodiments of the invention are also suitable for use with all quantitative compendia and photometric methods relating the reaction progress to endotoxin levels, including 1) kinetic chromogenic, where the time until the optical absorption changes by a specified amount is related to concentration, 2) endpoint chromogenic, where the optical absorption change over a fixed time is related to concentration, 3) kinetic turbidimetric, where the time until the turbidity (usually measured by optical absorption) changes by a specified amount is related to concentration, and 4) endpoint turbidimetric, where the turbidity change over a fixed time is related to concentration. The microfluidic disc enables the user to perform at least two simple or unadulterated analyses and at least two spiked analyses on each measurement sample, and at least two analyses of standards and blanks (calibration samples). This may be accomplished by having a reservoir portion in the microfluidic disc for each fluid sample and a distribution network to at least four areas where samples may be precisely metered into exact volumes.

As used in this specification, the term "fluid sample" may include not only the sample to be analyzed ("measurement sample"), but water that shows no reaction with the endotoxin detection reagent or lysate employed at the detection limit. Samples of non-reactive water may also be referred to as "blanks", "LAL Reagent Water", "Water for BET" or "Water for Injection". The term "fluid sample" may also include solutions comprising a prepared solution comprising reagents, standards, spikes, or a prepared detection reagent. Reagent, as used herein, is used broadly and includes any substance chemical, or solution that is used the laboratory to detect, measure, otherwise examine substances, chemicals, or solutions, or aid in such examination. Reagent includes standards and detection reagents. Suitable detection reagents for LAL-reactive substances include LAL reagent, recombinant Factor C reagent, a mixture of recombinant Factor C and LAL reagent, and preparations that include sushi peptides, sushi peptide fragments, sushi peptide dimers, and other specific binding proteins such as antibodies and receptor binding proteins derived from bacteriophages. The term "fluid sample" may also include prepared solutions of endotoxin or glucan standard ("LAL-reactive substance" or "standard"). Each fluid sample type listed above may have its own reservoir portion or two or more of the fluid sample types may share at least one introduction port.

The disc enables the user to combine and mix metered samples and any reagents or standards that may be present. The disc may also have one or more optical chambers and may be inserted into an optical reader to measure optical changes in the fluid samples.

The microfluidic disc may also contain similar structures for the analysis of blanks and standards that do not contain a distribution network for the sample, so that a standard or blank and reagent are the fluids mixed and analyzed. At least three standards at different levels may be analyzed, with each standard and the blank having the means of being analyzed in at least three replicates from a single sample. Thus the disc supports analysis, in triplicate, of calibration standards at three different levels and a blank. The disc as described above allows for all the tests required by the compendia to be performed in one disc using the same sample.

In one embodiment, the measurement samples, reagents, and standards may all be introduced as prepared liquids ready for use. A single fluid sample of each type may be introduced to the disposable apparatus and then distributed.

In another embodiment, blank water may be used for the blank analysis and to distribute and dilute a single standard at the highest level. Thus, the standard is diluted as necessary by distribution, precise metering, and mixing to produce the other standards or spikes.

In yet another embodiment, the disc may be pre-loaded with standard, reagent, or mixtures thereof. The standards may be isolated in portions of the disc as a liquid or dried preparation that may be diluted or reconstituted. This eliminates the need for a standard introduction port. The isolated standards may be distributed or used directly in the mixing or analysis portions of the apparatus. For standard analyses, the standards are mixed with blank water and then distributed or used directly. For spikes, the standard may be reconstituted with sample, reagent, or a mixture of the two.

The reagent may also be isolated in the disc as a liquid or dried preparation, such that it may be diluted or reconstituted with blank water, and then distributed and used. This blank water may be sourced from the same reservoir as the analyzed blanks. The reagent may be isolated in each mixing area or other area unique to each analysis for reconstitution with blank water, sample, or both.

Alternatively, both the reagent and standards may be isolated in the disc. Thus, only samples and blank water need be added to the apparatus for analysis. It should also be noted that when the detection or LAL reagent is immobilized in a dry form, it may be reconstituted with samples or standards instead of blank water, increasing the relative concentration of the material to be analyzed and increasing the speed and sensitivity of the assay.

In one aspect of the invention, a microfluidic disc for use with a centripetal microfluidics system is disclosed. The microfluidic disc may comprise at least two testing areas wherein each testing area includes a reservoir portion for receiving at least one fluid sample. The reservoir portion may comprise a reservoir and a reservoir outlet. The disc may comprise a distribution network portion in fluid communication with the reservoir portion. Each distribution network portion may comprise a distribution network of at least four (4) testing channels, wherein each testing channel has a metering portion and at least one analysis chamber portion. The metering portion may be sized to meter an aliquot of the fluid sample for analysis in the analysis chamber portion. At least one testing channel portion has at least one reagent isolated therein. The reagent may comprise a LAL-reactive substance.

In another embodiment of the disc, at least one distribution network is a calibration network comprising at least eight (8) testing channels. At least two (2) of the channels have no LAL-reactive substance therein. At least two (2) of the channels have a first amount of a LAL-reactive substance isolated therein. At least two (2) of said channels have a second amount of a LAL-reactive substance isolated therein, and at least two (2) of the channels have a third amount of a LAL-reactive substance isolated therein.

In yet another embodiment of the disc, at least one distribution network is a sample measurement network comprising at least four (4) testing channels. At least two (2) of the channels have no LAL-reactive substance therein and at least two (2) of the channels have a spike with a fourth amount of a LAL-reactive substance isolated therein.

In another embodiment of the microfluidic disc, at least one valve may be positioned between a) the reservoir portion and the distribution network portion and/or b) the metering portion and the analysis chamber portion. The valve may be configured to allow centrifugal forces to motivate the aliquot to flow across the valve from the metering portion to the analysis chamber portion.

In yet another embodiment, all of the analysis chamber portions may comprise a mixing chamber and an optical chamber. The mixing chamber may have at least one additional reagent isolated therein. The additional reagent may comprise a detection reagent. The mixing chamber may have thick sidewalls optimized for mixing the detection reagent immobilized on the sidewalls with the aliquot. The thick sidewalls may promote flow paths that mix the reagents and the aliquot close to the thick sidewalls. In another embodiment, the analysis chamber may be configured to enable mixing the aliquot with the reagent using at least one of the Coriolis effect, inertial effect, or bubbles and/or beads entrained therein.

In yet another embodiment, the distribution network portion may further comprise a main distribution channel, a waste inlet channel, and a waste chamber for confining any excess fluid sample and separating the excess from the aliquot. In another embodiment, the disc may be configured to allow centrifugal forces to eliminate bubbles from the sample fluid in the optical chamber portion.

In another embodiment, a reader configured to test fluid samples in a microfluidic disc is disclosed. The reader may comprise an enclosure, an optical bench, a centripetal disc drive, and a controller. The microfluidic disc may comprise at least two testing areas wherein each testing area includes a reservoir portion for receiving at least one fluid sample. The reservoir portion may comprise a reservoir and a reservoir outlet. The disc may comprise a distribution network portion in fluid communication with the reservoir portion. Each distribution network portion may comprise a distribution network of at least four (4) channels, wherein each channel has a metering portion and at least one analysis chamber portion. The metering portion may be sized to meter an aliquot of the fluid sample for analysis in the analysis chamber portion.

In another aspect, the enclosure may include an inlet for inserting a fluid sample into a reservoir of the disc. The inlet and reader may be configured to prevent the user from inserting the fluid sample into an incorrect reservoir.

In yet another embodiment of the reader, at least one distribution network may be a calibration network comprising at least eight (8) testing channels. At least two (2) of the channels have no LAL-reactive substance therein. At least two (2) of the channels have a first amount of a LAL-reactive substance isolated therein. At least two (2) of the channels have a second amount of a LAL-reactive substance isolated therein, and at least two (2) of the channels have a third amount of a LAL-reactive substance isolated therein.

In another aspect of the reader, at least one distribution network may be a sample measurement network comprising at least four (4) testing channels. At least two (2) of the channels have no LAL-reactive substance therein, and at least two (2) of the channels have a spike with a fourth amount of a LAL-reactive substance isolated therein.

In yet another embodiment of the invention, a method for testing at least one fluid sample for LAL-reactive substances is disclosed. The method may comprise inserting a microfluidic disc into a optical reader. The microfluidic disc may comprise at least two testing areas wherein each testing area includes a reservoir portion for receiving at least one fluid sample. The reservoir portion may comprise a reservoir and a reservoir outlet. The disc may also comprise a distribution network portion in fluid communication with the reservoir portion. Each distribution network portion may comprise a distribution network of at least four (4) channels, wherein each channel has a metering portion and at least one analysis chamber portion comprising an optical chamber. The metering portion may be sized to meter an aliquot of the fluid sample for analysis in the optical chamber.

The reader may comprise an enclosure, an optical bench, a centripetal disc drive, an inlet for introducing said fluid sample into said disc, and a controller. A fluid sample is inserted into the inlet of the reader. The reader spins the disc until a reaction velocity is reached. The reader analyzes the aliquot in the optical chamber using the optical bench to obtain measurement data and/or reaction data. The measurement data and/or reaction data and calibration curves may be used to calculate testing results. The reader may then report and/or store the test results.

In another embodiment, at least one reagent comprising a detection reagent and/or LAL-reactive substance may be introduced into the reader inlet. The reader may spin the disc until reaction velocity is reached. The aliquot is allowed to react with the detection reagent. The aliquot may be analyzed in the optical chamber using the optical bench to obtain measurement data and/or reaction data. The measurement data and/or reaction data and calibration curves may be used to calculate testing results. The reader may then report and/or store the test results.

In another method embodiment, at least one testing channel has at least one reagent isolated therein. The reagent may comprise a LAL-reactive substance and/or a detection reagent. In yet another embodiment, the method may further comprise transferring the fluid sample from the reservoir to the metering portion and metering the aliquot. The aliquot may be transferred from the metering portion to the optical chamber. The aliquot may be continuously monitored in the optical chamber to obtain measurement data and/or reaction data using the optical bench until the aliquot has finished reacting. The measurement data and/or reaction data and calibration curves may be used to calculate testing results. The reader may then report and/or store the test results.

In another method embodiment, the measurement data and/or reaction data may comprise aliquot volumes, reaction kinetics, fluid motions, transmission, absorption, optical density, color, color value, hue, spectrum, turbidity, scattered light, chemiluminescence, fluorescence, and magnetic resonance. The method and/or said measurement data and/or reaction data may be validated using historical measurement data and/or data from known reaction kinetics. In yet another embodiment, a tracer may be immobilized within the analysis chamber to aid in measuring and validating the aliquot volume.

In yet another embodiment, a reader configured to test fluid samples in a microfluidic disc is disclosed. The reader may comprise: an enclosure, an optical bench, a centripetal disc drive, and a controller. The microfluidic disc may comprise at least two testing areas. Each testing area may include: a reservoir portion for receiving at least one fluid sample, the reservoir portion comprising a reservoir and a reservoir outlet; and a distribution network portion in fluid communication with the reservoir portion. Each distribution network portion may comprise a distribution network of at least four (4) testing channels. Each testing channel may have a metering portion and at least one analysis chamber portion, with the metering portion being sized to meter an aliquot of the fluid sample for analysis in the analysis chamber portion. The distribution network portion may further comprise a main distribution channel in fluid communication with the reservoir outlet, the metering portions are in fluid communication with the main distribution channel, a waste inlet channel in fluid communication with the main distribution channel, and a waste chamber in fluid communication with the waste inlet channel for confining any excess of the fluid sample and separating the excess fluid sample from the aliquot. The microfluidic disc may be removably securable to the centripetal disc drive within the enclosure, such that a measurement of changes in the at least one fluid sample may be taken, when each of the testing areas rotates through the optical bench. The rotation and the measurement may be controlled by the controller.

Advantages of the present invention will become more apparent to those skilled in the art from the following description of the embodiments of the invention which have been shown and described by way of illustration. As will be realized, the invention is capable of other and different embodiments, and its details are capable of modification in various respects.

BRIEF DESCRIPTION OF SEVERAL VIEWS OF THE DRAWINGS

These and other features of the present invention, and their advantages, are illustrated specifically in embodiments of the invention now to be described, by way of example, with reference to the accompanying diagrammatic drawings, in which.

Figure 1A:
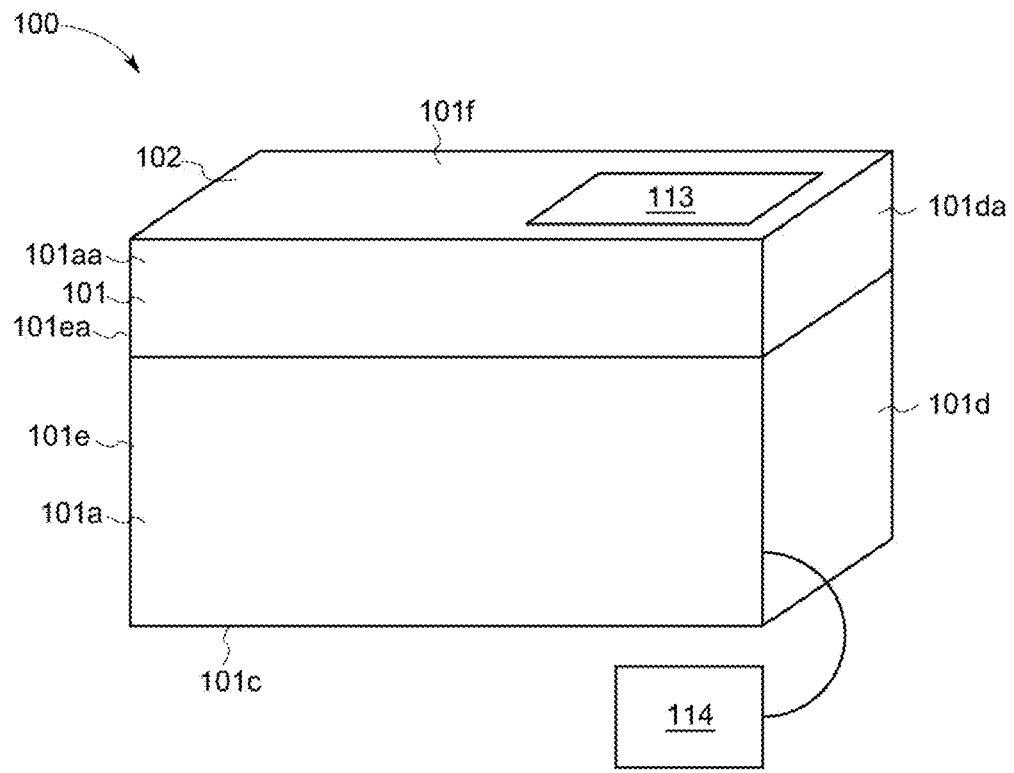
FIGS. 1A, 1B, 1C, and 1D are an exemplary embodiment of a reader for testing a plurality of fluid samples in a microfluidic disc.

It should be noted that all the drawings are diagrammatic and not drawn to scale. Relative dimensions and proportions of parts of these figures have been shown exaggerated or reduced in size for the sake of clarity and convenience in the drawings. The same reference numbers are generally used to refer to corresponding or similar features in the different embodiments. Accordingly, the drawing(s) and description are to be regarded as illustrative in nature and not as restrictive.

DETAILED DESCRIPTION

Embodiments of the invention improve the standard Bacterial Endotoxins Test ("BET") by the creation of specialized discs with endotoxin detection reagents and endotoxin standards preloaded into the disc and a reader for the discs. In another embodiment, a microfluidic disc 103 with endotoxin detection reagents and endotoxin standards preloaded into the optical chambers or mixing chambers are disclosed. In a further embodiment, a reader 100 for the microfluidic disc 103 is disclosed.

The disc and reader are designed to measure the BET in samples and to also provide calibration data from known endotoxin spikes. The preloaded test discs may be designed to meet all the current BET pharmaceutical regulations requirements. The disc and reader may be used with turbidimetric, chromogenic, and gel-clot BET methods. Suitable detection reagents for LAL-reactive substances include LAL reagent, recombinant Factor C reagent, a mixture of recombinant Factor C and LAL reagent, and preparations that include sushi peptides, sushi peptide fragments, sushi peptide dimers, and other specific binding proteins such as antibodies and receptor binding proteins derived from bacteriophages. Endotoxin standards include endotoxin that has been calibrated to the relevant regulatory master endotoxin.

Accordingly, the disclosed disc and reader significantly reduce the number of steps required to measure the BET in samples, thereby minimizing contamination, timing delays and mismatches, and thus, improving accuracy. The disc and reader are suitable for use with FDA-licensed LAL.

The disclosed disc and reader reduce sample preparation time significantly. By preloading the test reagents into the disc, tedious reagent addition for each sample is eliminated. Test reagents may be any reagent that aids in testing samples. Suitable test reagents include, but are not limited to endotoxin detection reagents and endotoxin standards. Suitable endotoxin detection reagents may comprise Amoebocyte Lysate. Endotoxin standards may be a USP Endotoxin Reference Standard that has been calibrated to the current World Health Organization International Standard for Endotoxin. The accuracy of the test may also improved by minimizing timing and pipetting errors. Sample introduction errors may be further reduced by a plurality of optional identification mechanisms on the reader and disc that identifies the sample to the user or notifies the user if additional reagents are required. Suitable identification mechanisms may include optical markers such as color markers, alphanumeric markers, or light emitting diodes.

The test reagents may be deposited onto various surfaces of the disc, such as onto the interior surfaces of an optical chamber or at points of fluid flow in a mixing chamber to allow a sample, standard, or blank measurement, onto a soluble coating, or onto an optically transparent, translucent or reflective insoluble film. Alternatively, the test reagents may be added as a pellet, dried beads or coarse particles, or deposited into a carrier media that is added to the disc.

The disc with preloaded reagents may be packaged such that it is sealed from the environment by using a barrier material that prevents moisture, bacteria, and LAL-reactive substances from contaminating the preloaded reagents. The packaging may also include agents that active reduce moisture, oxygen and/or volatile contaminants. Exemplary agents include, but are not limited to silica gel, for moisture, iron oxide packets for oxygen, and activated carbon for volatile contaminants. In one embodiment, the barrier material is a clean bag.

In one embodiment, a disc is disclosed wherein the disc has been preloaded with at least one test reagent. In another embodiment, the test reagent may comprise an endotoxin standard. In another embodiment, the endotoxin standard may be present in a plurality of concentrations, wherein each concentration is present on a separate portion of the disc. The concentrations may be a multiple of the lowest concentration for the turbidimetric or chromogenic technique. In yet another embodiment, the test reagent may comprise an endotoxin detection reagent. In another embodiment, the endotoxin detection reagent may be *Limulus* Amoebocyte Lysate.

When the spike is made from dried standard, the volumes of the sample and reagent are identical to the other analysis and calibration tests. When the spike is liquid, it can be added as a "hot spike" which is an accepted method in the industry, recommended by manufacturers, and accepted by regulators. In this method, a solution of standard 10 times the spike concentration desired is added to a sample of full volume as 10% of that volume. The standard amount of LAL reagent is added, and the resulting mixture monitored in a cell with a pathlength 5% longer than a standard non-spiked well's. This mimics the hot-spiking method used in microplates, where the volume of combined samples and reagent, and thus the optical column and pathlength, is 5% greater with hot spiked samples.

As used in this specification, the term "sample" may include not only the sample to be analyzed, but water that shows no reaction with the endotoxin detection reagent or lysate employed at the detection limit. Samples of non-reactive water may also be referred to as "LAL Reagent Water" or "LWR".

Figure 1B:
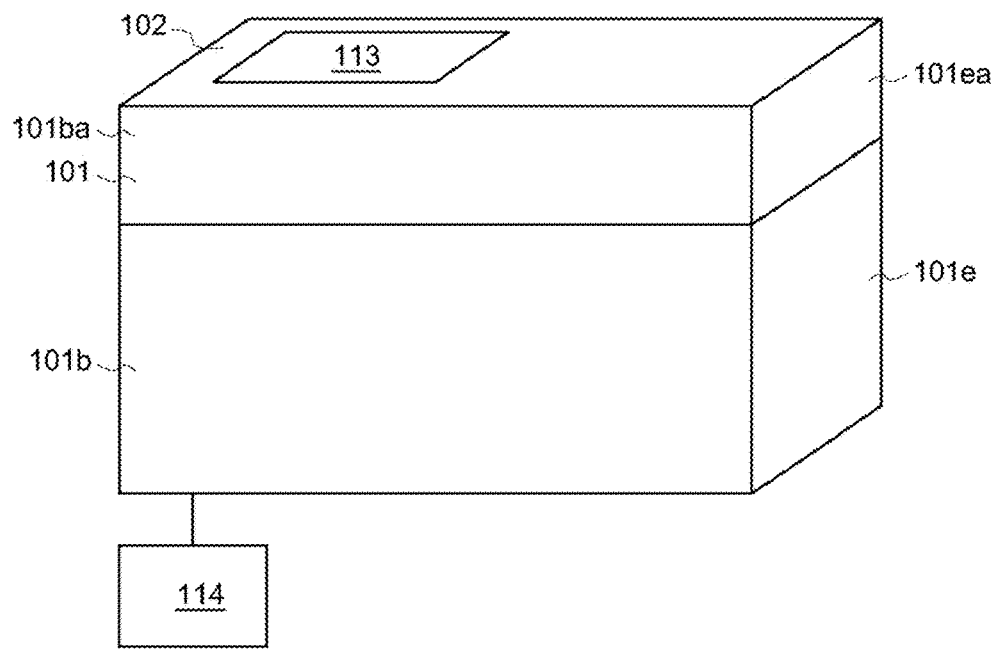

Referring to FIGS. 1A and 1B, an exemplary embodiment of reader 100 for use in testing fluid samples is shown. Reader 100 is has an enclosure 101 made from an opaque and insulating material that isolates the interior 101g of reader 100 from outside light and environmental effects such as temperature. As can be seen, reader 100 is designed to be compact due to the simplicity of rotational control and monitoring.

Enclosure 101 is comprised of a front wall 101*a*, rear wall 101*b*, bottom wall 101*c*, right wall 101*d*, left wall 101*e*, and top wall 101*f*, which define the interior 101*g* of reader 100. The top wall 101*f* and upper sections of front wall 101*aa*, rear wall 101*ba*, right wall 101*da*, left wall 101*ea* of enclosure 101 define lid 102, which allows a user to access the interior of reader 100 for insertion and removal of the disc 103 containing fluid samples. However, it is anticipated that in other embodiments of reader 100, access to the interior of reader 100 may be provided by other structures, including, but not limited to a door in top wall 101*f*. Further, as can be seen, reader 100 is further comprised of a user interface 113 and/or input device 114, such as a computer.

Figure 1C:
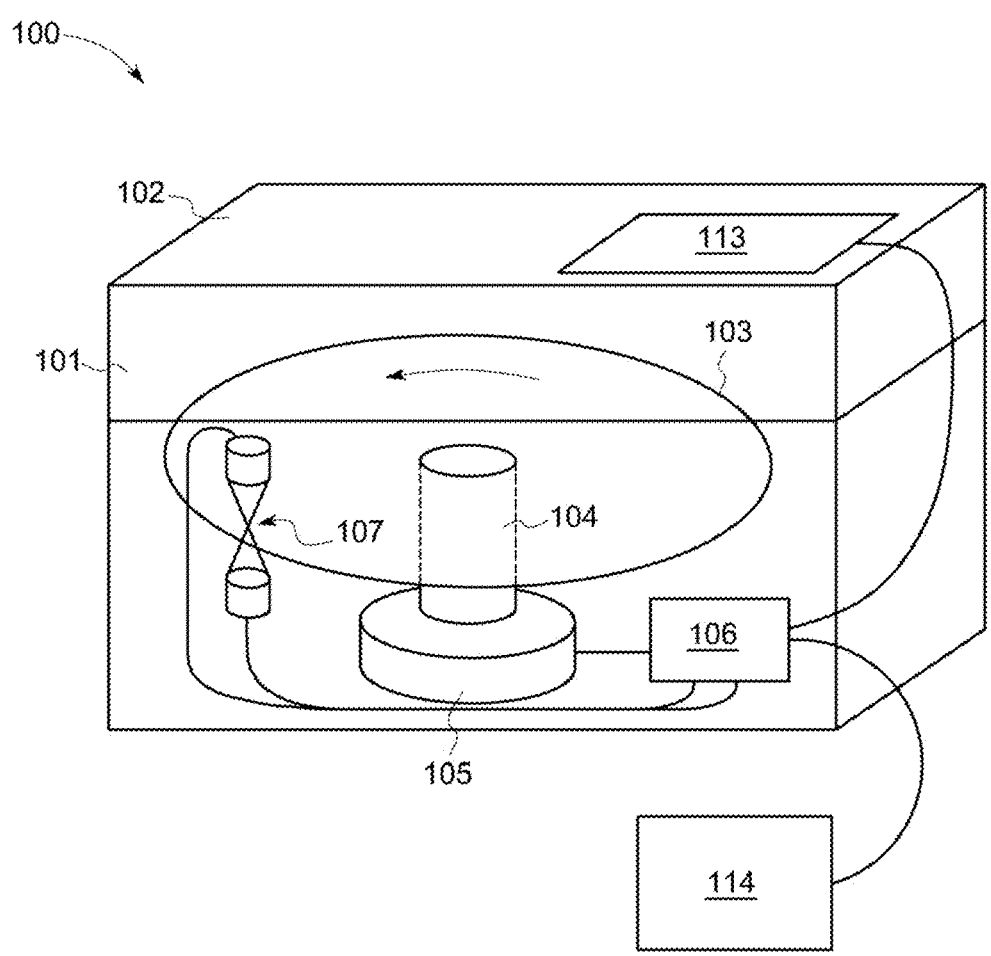
Figure 1D:
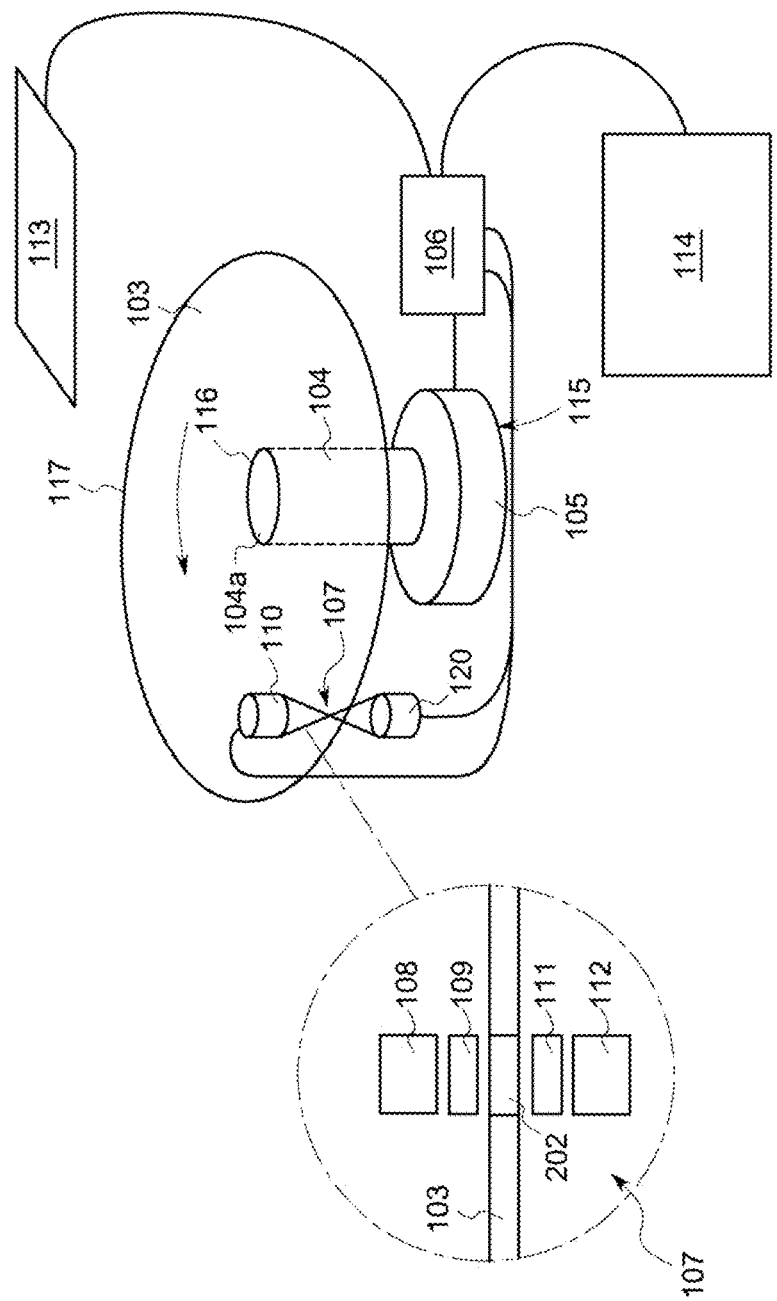

Turning to FIGS. 1C and 1D, in FIG. 1C, interior contents of reader 100 are shown through enclosure 101 to demonstrate an exemplary configuration of the contents of reader 100 within enclosure 101. FIG. 1D shows the interior contents of reader 100 without enclosure 101. The interior components of reader 100 are comprised of optical bench 107, disc 103, controller 106, and centripetal disc drive 115. Centripetal disc drive 115 is comprised of motor 105 which rotates spindle 104. Disc 103 is removably secured to the upper portion 104*a* of spindle 104 and is rotated by motor 105. Optical bench 107 is comprised of source 110 and detector 120. User interface 113, input device 114, motor 105, and optical bench 107 are controlled by and interact with controller 106.

Disc 103 has microfluidics, described below, which contain immobilized reagents. Disc 103 also has a hub 116, which is removably secured to the upper portion 104*a* of spindle 104. Hub 116 can be a hole or other type of interface that can be removably secured to spindle 104, thereby allowing disc 103 to be spun by motor 105. It is anticipated that motor 105 can be any type of mechanical actuator that is capable of rotating disc 103.

Individual optical chambers 202 arranged at the outer edge 117 of disc 103 are optically monitored by the optical bench 107. Optical bench 107 measures the light absorbed in optical chambers as they pass source 110 and detector 120, while disc 103 is rotated. Source 110 is comprised of light source 108, which could be, but is not limited to, Light Emitting Diodes (LEDs) which have a controlled spectral output. Light source 108 could also be, but is not limited to, a monochrometer that supplies a narrow spectral range by using devices which split light by its spectrum and excludes those frequencies outside of the needed band. The light source 108 can also be configured so multiple optical sources of different types, a single optical source of variable wavelengths, or other method of using multiple light bands to increase signal or reduce interference and noise. For example, monitoring at multiple frequencies for a change in optical density could reduce the interference of unstable sample color. This could also be done using separate optical sources and detectors in different reader locations. Source 110 is further comprised of source optical elements 109, which can shape, form or filter this light to produce a more-ideal optical system or limit interference. Source optical elements 109 can include, but are not limited to, apertures, band pass or other optical filters, diffraction gratings, diffusers, lenses, optical fibers or other light guides, mirrors, or other such components.

Detector 120 is comprised of a light detector 112 and detector optical elements 111. Detector optical elements 111, which can shape, form or filter the light before it is received by light detector 112 to produce a more-ideal optical system or limit interference. Detector optical elements 111 can include, but are not limited to, apertures, band pass or other optical filters, diffraction gratings, diffusers, lenses, optical fibers or other light guides, mirrors, or other such components.

Further, light detector 112 can be, but is not limited to, a photodiode or photomultiplier tube. Light detector 112 measures the intensity of the light passing through optical chambers 202 the disc 103. This intensity can be used to calculate the optical absorbance of the fluid in each optical chamber 202 over the spectrum specified by the source 110, detector 120, source optical elements 109, and/or detector optical elements 111. This is done by controlling source 110 and detector 120, and logging the output of detector 120 using the controller 106. Comparisons with the light received by detector 120 at full intensity or with the initial conditions within chambers 202 before a reaction takes place within chambers 202 can be used to generate objective absorptions (also known as optical density) to be used in for monitoring the LAL reaction. Reference values for zero light transmission (an area on the disc which fully blocks the light) or zero absorption (an open path with no fluid or no disc material) can also be used to objectively calibrate the response of the optical bench and disc materials. Light is received by detector 120 at full intensity when the light received by detector 120 passes through an optical chamber 202 that does not contain any fluid, contains an unreacted sample, or contains an unreacted sample with reagent. In another embodiment, when a duplicate of optical bench 107 is present within enclosure 101 and a disc 103 is not present between the source 110 and detector 120 of the duplicate of optical bench 107, the light provided by source 110 to detector 120 is the full intensity of light can also be received by detector 120.

The light then passes through an optical chamber 202 in disc 103, which is typically moving through the beam of light formed by 108 and 109 if present. Optical chamber 202 has an internal volume that can be filled with sample and reagents, two optical windows 205 on either side of the face of disc 103 are transparent at the light frequencies sensed by detector 120. As can be seen, optical windows 205 create a path through optical chamber 202 by which the light produced by source 110 can travel, be absorbed by the contents of optical chamber 202, and be received by detector 120. Optical components such as windows, dark fields, apertures, lenses, reflectors, or diffusers can also be incorporated into the optical chamber itself to provide part of the optical path or increase the system's stability or sensitivity. The beam of light produced by source 110 can then be further modified or focused by more optical elements 111, which include the list for 109 and can limit the field of view or spectrum, or otherwise be used to improve or regulate the response of the optical system.

In another aspect of the reader and microfluidic disc, the sensing method is any of a variety of optical measurements, including transmission, absorption, optical density, color, color value, hue, spectrum, turbidity, scattered light, chemiluminescence, and fluorescence. In another aspect of the reader and microfluidic disc, the sensing method is method capable of sensing changes in the fluid remotely in a spinning disc, including more-complex optical methods such as Raman spectroscopy, nuclear magnetic resonance, and surface plasmon resonance, and non-optical methods such as electrical capacitance, magnetism, sonic resistance, and sonic refraction.

The reader can be monitored and controlled with a user interface (typically graphical) 113 on or near the reader, or any remote controller, PC, or other input/output device 114. This would allow data input, data acquisition, data logging, user control, user interface, and all necessary security and traceability to meet compendia requirements (the specifications made by regulatory agencies via pharmaceutical compendia).

The method for placing samples in the disc is not shown. However, it is contemplated that samples could be placed in disc 103 contained in reader 100 by many methods, including, but not limited to, injection from a pipette into labeled ports, but would best be done under reader control with means to prevent mistakes, such as by providing a single sample access port or door in the top wall 101f of reader 100, and having the reader 100 align disc 103 so that only the correct reservoir 325 of disc 103 can be accessed when a sample is added through reader 100. There are many ways of doing this, but all require that reader 100 know the position of the disc 103. Further, it is also necessary for reader 100 to know the position of disc 103 in order to accurately match the optical measurement results with the samples in chambers 202 of disc 103. It is anticipated that the position of the disc 103 can be ascertained by many methods, including, but not limited to encoders, marks, windows, or mirrors on hub that can be sensed, magnets or charges that can be monitored, direct monitoring of the hub, spindle, or motor positions and a means of limiting the mounting of the disc to one position on the hub, monitoring of the motor drive signal to ascertain the amount it should move, or monitoring of the optical signal from 107. Another method of determining the position of disc 103 is shown in US Patent Application Publication 20090139578, filed on Jul. 30, 2008, published on Jun. 4, 2009, and entitled "CENTRIFUGAL FORCE BASED PLATFORM, MICROFLUIDIC SYSTEM INCLUDING THE SAME, AND METHOD OF DETERMINING HOME POSITION OF THE PLATFORM", which is herein incorporated by reference.

Further, it is contemplated that in some embodiments of reader 100 and disc 103, the position of disc 103 would be determined and controlled for reading and sample loading by reader 100 through the use of an optical method. This optical method can be incorporated into the main optical path, such as by using a single optical chamber 202 having opaque optical windows 205 in conjunction with optical bench 107 or a separate optical path. Further, it is contemplated that in other embodiments of disc 103 and reader 100, the position of disc 103 can be determined using non-optical means, such as a magnet and sensor.

It is contemplated that in some embodiments of reader 100, the position of disc 103 can be determined using a combination of methods described above. For example, a single mark or pattern disruption present on disc 103, which would indicate when one position on the disc had been reached, could be used in conjunction with keeping track of the number of pulses sent to motor 105, which under normal conditions would indicate position. By monitoring both the single mark or pattern disruption on disc 103 the number of pulses sent to motor 105, any "lost steps" can be compensated for, giving an accurate approximation of the position of disc 103 within reader 100 at any time.

In an embodiment, reader 100 includes fixed optical components. The fixed optical components may include low cost LEDs and photodiodes. Reader 100 can include bandpass filters to increase the accuracy of optical measurements. The reader can also be modulated or electronically chopped to provide a reduction in optical noise, reject ambient light, and reject stray light. As can be seen, it is contemplated that reader 100 includes a small number of optical components, which result in a lower cost optical bench 107, while using of higher quality parts.

Further, in some embodiments of reader 100, optical bench 107 can use optical chopping, which increases the signal to noise ratio of detection by reducing the effect of 1/f noise (baseline drift). The chopping can be from a modulated source (e.g., LEDs turned on and off repeatedly) or it can be from mechanical chopping (light blocked and unblocked mechanically). The spinning disc 103 provides a natural chopping signal as each optical chamber 202 moves through optical bench 107. Further the signal to noise ratio can also be increased by digitally filtering the output of optical bench 107.

The fluid to be tested in disc 103 can be injected into reservoir 325 by way of a pipette or any other injection apparatus that can accurately measure and deliver the measured volume of sample fluid. It should be understood that precise measurement of fluid to be introduced into each reservoir 325 is not necessary, provided more fluid—and not less fluid—than necessary for testing is added to reservoirs 325. In an embodiment, a pre-determined volume of fluid is introduced into reservoir 325 for testing. In another embodiment, reservoir 325 is completely filled with fluid to be tested without precisely measuring the volume of fluid introduced into reservoir 325.

Figure 1E:
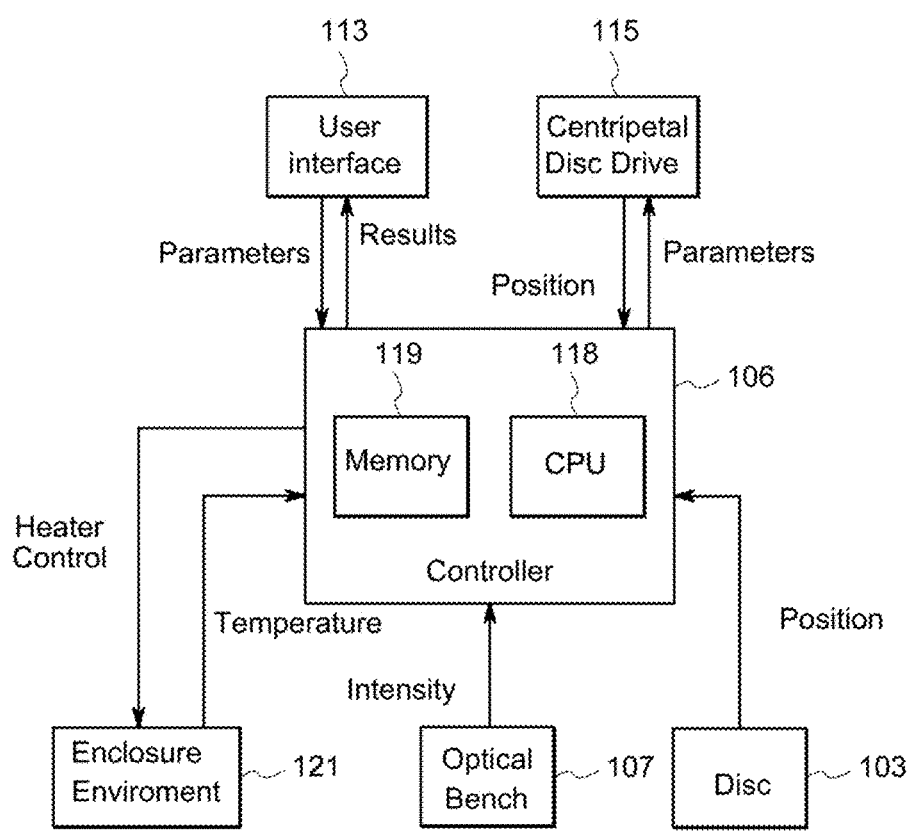
FIG. 1E is a block diagram depicting the circuitry of an exemplary embodiment of a reader.

FIG. 1E is a block diagram of the components that interact with controller 106. As can be seen, controller 106 is comprised of memory 119 and a CPU 118 to execute the program stored in memory 119. Controller interfaces with user interface 113, centripetal disc drive 115, disc 103, optical bench 107, and enclosure environmental augmenters 121. In some embodiments, input/output device 114 also interacts with controller 106.

In one embodiment, enclosure environmental augmenters are comprised of a heater and thermometer for regulating the temperature within enclosure 101. Disc 103 provides position information to controller 106. Optical bench 107 provides controller 106 with information regarding the intensity of light received by detector 120. Enclosure environment augmenters 121 provide a measurement of the temperature within enclosure 101 to controller 106, and controller 106 uses this information to determine whether heater should be activated within enclosure 101. User interface 113 allows a user to provide controller 106 with test parameters and allows controller 106 to display test results to user. Centripetal disc drive 115 provides position information to controller 116 and also permits controller 106 to regulate the rotation of disc 103.

Figure 1F:
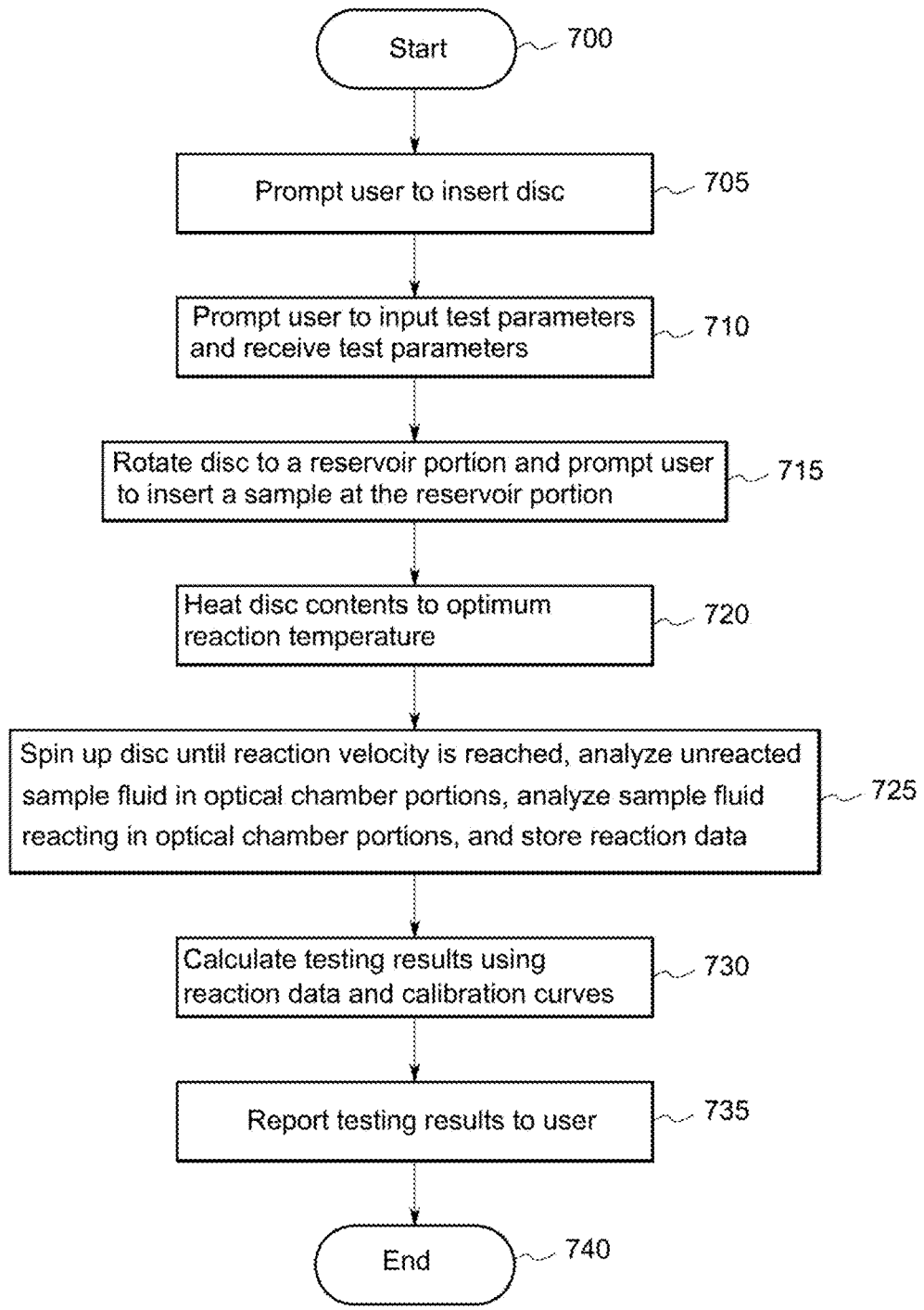
FIG. 1F is a flowchart of the program executed by CPU of an exemplary embodiment of a reader.

FIG. 1F is a flowchart of the program stored within memory 119 and executed by CPU 118 of reader 100. In step 700 the CPU 118 initializes and retrieves the program of FIG. 1F from memory 119. In step 705 the user is prompted via user interface 113 to insert disc 103 into reader 100. Once the user inserts disc 103 into reader 100 and closes reader 100, the user is prompted in step 710 via user interface 113 to insert test parameters. Once CPU 118 receives the test parameters, the disc is rotated in step 715 such that a reservoir portion 620 is lined up with an inlet or port in the lid 102 of reader 100, which only allows the user to insert a sample into the correct reservoir portion 620 of disc 103. The user is prompted and instructed via user interface 113 as to what sample to insert. Once the sample is inserted, CPU 118 instructs centripetal disc drive 115 to rotate the disc to the next sample reservoir portion and again prompts and instructs the user as to which sample to insert, and repeats the process until all of the samples have been inserted into disc 103. In some embodiments that use liquid reagents, CPU will also lineup an inlet or port in the lid 102 with reservoir portion 620 and prompt and instruct the user via a user interface 113 as to what reagent to insert into reservoir portion 620.

In step 720, the disc contents are heated to optimum reaction temperature within enclosure 101 of reader 100. CPU 118 achieves and maintains the optimum reaction temperature using a heater and thermometer. Once all of the samples and reagents are loaded into reservoir portions 620 of disc 103 and the enclosure 101 is at optimum reaction temperature, in step 725, CPU 118 instructs the centripetal disc drive 115 to spin disc 103 up until reaction velocity is reached. The reaction velocity is the rotational velocity at which all necessary fluids move into the analysis or optical chamber. The reaction velocity may be a specific velocity or a series of discrete velocities depending on the details of the fluidics and mechanisms of fluid motion. If a series of discrete velocities are required, changes in velocities may be made by increasing the speed of the spinning disc to increase velocities and to move the fluid outward. Velocities may also be varied by applying alternating high and low forces to the disc to utilize siphon valves. Once reaction velocity is reached, sample fluid has flowed from reservoir portion 620 into optical chamber portions 635 and the sample fluid is analyzed in the optical chamber portions 635 before the fluid reacts with reagents in optical chamber portions 635. Further, in step 725, the sample fluid is analyzed while reacting in optical chamber portions 635. The analysis information collected in this step, also known as reaction data, is stored in memory 119.

Once the reaction data is stored in memory 119, in step 730 CPU retrieves the reaction data, uses the reaction data to create calibration curves, and then uses the reaction data and calibration curves to calculate testing results. The testing results are reported to the user in step 735 via user interface 113. Following step 735, the program ends at step 740.

Figure 2:
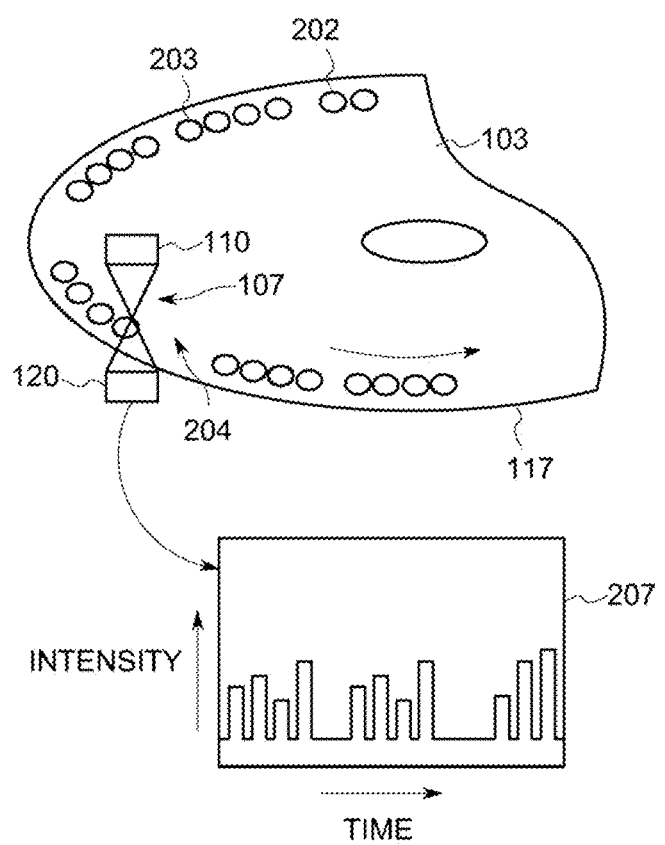
FIG. 2 depicts the dynamic monitoring of absorption of samples in optical chambers of microfluidic disc by reader in accordance with an exemplary embodiment of the present invention.

FIG. 2 depicts the dynamic monitoring of absorption of samples in optical chambers 202 of disc 103 by reader 100. As can be seen, the spinning microfluidics disc 103 includes optical chambers 202 near the outer edge 117 of disc 103. Optical chambers 202 spin through optical bench 107. Optical chambers 202 can be spaced in regular or irregular intervals. It is contemplated that in some embodiments of disc 103, the spacing intervals of optical chambers 202 can be of different sizes, which can be used to encode position information for disc 103 into the output of optical bench 107. For example, as is shown in FIG. 2, there can be small gaps 203 and larger gaps 204 between chambers 202 or groups of chambers 202. The small gaps 203 and larger gaps 204, will produce corresponding large and small gaps in the data stream of optical bench 107. These gaps in the data stream are created when light produced by source 110 is received and transformed by detector 120 into an electrical signal.

An exemplary data stream is shown as intensity vs. time on a chart 207. The intensity of the light going through each optical chamber 202 is logged as a peak with the gaps in the optical chambers having no such peaks. The pattern of these gaps (or a single gap or reference chamber) can then be interpreted by the controller to determine position, possibly along with other information as detailed above. As can be seen in chart 207, one is clearly able to differentiate between the time periods when a small gap 203, large gap 204, or optical chamber 202 of disc 103 is passing through optical bench 107 based on the intensity of light received and transformed by detector 120. It is understood that in other embodiments, depending on the light transmission properties of the material of disc 103 present between optical chambers 202 and the configuration of optical bench 107, that gaps can be logged as a peak and light going through each optical chamber 202 can be interpreted as a valley. This is acceptable because one would still clearly be able to differentiate between the time periods when a small gap 203, large gap 204, or optical chamber 202 of disc 103 is passing through optical bench 107 based on the intensity of light received and transformed by detector 120.

Figure 7:
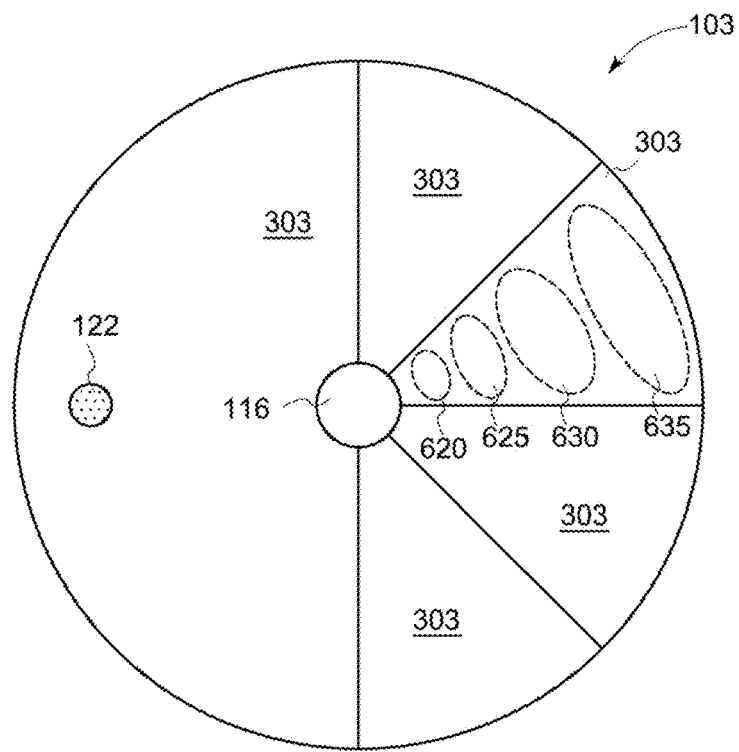
FIG. 7 is an exemplary schematic of a microfluidic disc.

FIG. 7 shows a schematic of disc 103 having hub 116, index mark 122, and a plurality of radial testing areas 303 around the entirety of disc 103. Index mark 122 allows reader 100 to ascertain the position of disc 103. Further, radial testing areas has a fluidics network 600 comprised of a reservoir portion 620, distribution network portion 625, metering portion 630, and optical chamber portion 635. Reservoir portion 620 is in fluid communication and upstream of distribution network portion 625, which is in fluid communication and upstream of metering portion 630, which is in fluid communication with and upstream of optical chamber portion 635. Reservoir portion 620 retains sample fluid until the rotational velocity of disc 103 sends the sample fluid to distribution portion 625, which distributes the sample fluid to the various aliquoting fluidics in metering portion 630. The aliquots created in metering portion 630 are sent to optical chamber portion 635 where reagent is mixed with the sample fluid and the reaction is analyzed.

It is understood that in some embodiments, reservoir portion 620, distribution network portion 625, metering portion 630, and optical chamber portion 635 may overlap. For example, it is anticipated that in some embodiments of fluidics network 600, the fluidics in network portion 625 and optical chamber portion 635 can form aliquots. Further, it is understood that valves may be present between reservoir portion 620, distribution network portion 625, metering portion 630, and optical chamber portion. Exemplary embodiments of valves include burst valves, siphon valves, passive valves generated by hydrophobic surface utilizing plasma etching, hydrophobic porous membranes, and mechanical valves.

Figure 3:
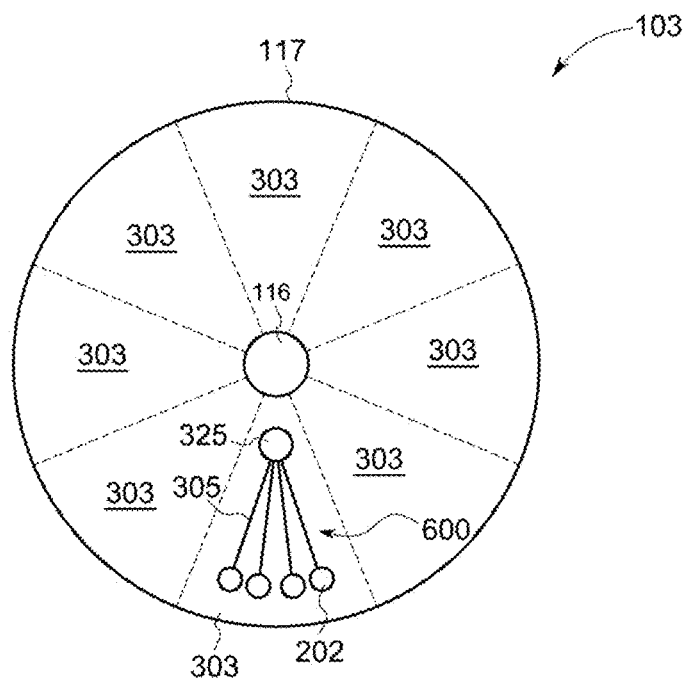
FIG. 3 is an exemplary embodiment of a microfluidic disc.

FIG. 3 shows a layout of an embodiment of microfluidic disc 103 having a hole for the hub 116 in the center of disc 103 for removably mounting to spindle 104 of reader 100. Individual samples, portions of samples, references or controls, or portions of references or controls, are analyzed by groups of optical chambers 202 segregated into testing areas 303. In typical embodiments of disc 103, radial testing areas 303 are laid out in a radial pattern. However, it is anticipated that a person having ordinary skill in the art can choose another pattern. Samples or references are placed in reservoirs 325, nearer the hub 116 of disc 103. When the disc 103 is spun, the fluid will move through open distribution channels 305 towards the outer edge 117 of disc 103. In some embodiments, distribution channels 305 also include chambers that can measure-out or aliquot the samples as they move towards the optical chambers 202. Various types of distribution channels, or channels, are referred to in this specification. The types include main distribution channels, waste inlet channels, aliquoting inlet channel, optical chamber inlet channel, etc. The various types of channels are described elsewhere in the specification.

In most embodiments of disc 103, the sample inserted into reservoirs 325 will typically be split into four aliquots, with each aliquot being delivered to a separate optical chamber 202. This is due to the fact that current compendia requirements are for each sample to be analyzed four times, twice without addition, and twice with a positive control added. This is also convenient for calibration and negative control analyses, because the "universal" implementation of these may require twelve (12) analyses using LAL Reagent Water as the sample, which can easily be accomplished by 3 sets of 4 analyses using the same layout, in which three reservoirs 325 would be provided with the sample, and the sample in each reservoir 325 would be split into four aliquots and provided to individual optical chambers 202, thereby creating the necessary twelve (12) analyses. It is contemplated that some embodiments of disc 103 may employ a 12-wide layout from a single, larger reservoir 325 in which a single reservoir 325 would be provided with the sample, and the sample would be split into twelve aliquots and provided to individual optical chambers 202, thereby creating the necessary twelve (12) analyses. It is envisioned that reservoir 325 in embodiments which provides samples to 12 analyses will be larger than reservoir 325 in embodiments that provides samples to four analyses.

In some embodiments of disc 103, valves control the flow of fluid in fluidics network 600. Valves could be implemented to perform such actions as stop the flow of fluid temporarily or permanently to regulate the flow of fluid through and reaction process taking place in disc 103. One type of valve is a burst valve. A burst valve uses the channel surface energy and capillary force to control fluid flow. It is known that capillary action transports fluid by wicking or otherwise drawing the fluid up small channels. The surface tension of the fluid provides the motivating force because the fluid wants to wet the channel walls, thereby the fluid draws itself up the channel until the pressure in the channel equals the surface tension motivating force. The same surface tension force can also be used to keep fluids from flowing through channels by constructing the channel out of a hydrophobic material or coat the walls of the channel with a hydrophobic material, instead of a hydrophilic material. Hydrophobic materials repel water and hydrophilic materials attract water (are wetting). One exemplary hydrophobic material is a hydrophobic micro-porous membrane, which, due to the material pore size, allows air to pass through, but not water. The small size of the hydrophobic micro-porous membrane pores require a large pressure, in the form of capillary pressure, to force water through the pores. This capillary pressure is dependent on the surface energy of the fluid in the channel, the surface energy of the channel material or interior channel coating, and the size and geometry of the channel. In another disc embodiment, siphon valves may be used.

Disc 103 may be made of a variety of materials including, but not limited to, polystyrene, cyclic olefin copolymer, and glycol-modified polyethylene terephtalate. In some embodiments of disc 103, carbon may be added to make the polystyrene black to aid in optical absorbance methods.

In FIG. 3, reservoir portion 625 is comprised of reservoir 325. Further, distribution network portion 625 is comprised of distribution channels 305. Further, metering portion 630 is comprised of distribution channels 305 and optical chamber 202. Lastly, optical chamber portion 635 is comprised of optical chamber 202.

Figure 4:
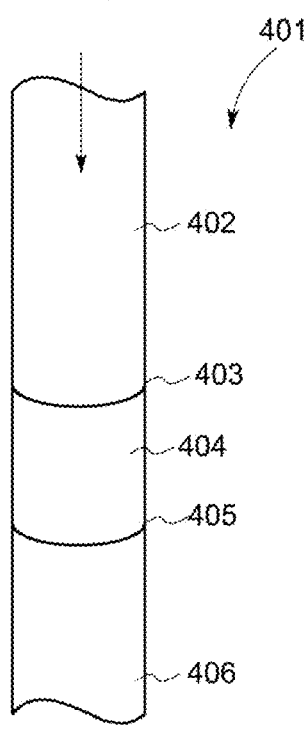
FIG. 4 is an exemplary embodiment of a burst valve.

FIG. 4 depicts an embodiment of a channel 401 having a burst valve 404. As can be seen, channel 401 is comprised of an upstream section 402, burst valve 404, and downstream section 406. Channel 401 has a wall made of or coated with different materials with different surface energies along its length. Upstream section 402 and downstream section 406 are hydrophilic, that is easily wet, and burst valve 404 is hydrophobic, hard to wet. Water traveling through channel 401 from upstream to downstream (in the direction of the arrow) will be drawn by capillary forces, centrifugal forces, pressure from upstream, or vacuum from downstream, to the upstream interface 403 where upstream section 402 and burst valve 404 meet. The pressure necessary for the fluid to move beyond upstream interface 403 will be the difference between the capillary pressure of burst valve 404 and the capillary pressure of upstream section 402. If the difference is greater than the motivating force of the fluid, the fluid will not flow past upstream interface 403 until the pressure difference is overcome, such as by spinning disc 103 faster. Once the fluid flows past the downstream interface 405, where burst valve 404 and downstream section 406 meet, the capillary pressure returns to what it originally was and the burst valve 404 no longer has any effect on the fluid flow or pressure in channel.

Alternatively, a burst valve can be constructed using material of a uniform surface energy and changing the diameter or geometry of the channel. In these cases, the channel typically opens up into a much larger chamber that has a low or zero capillary force due to its size.

Other valves can be used in disc 103, include, but not limited to passive siphons, vents, check valves, chambers, relief valves, wicks, or hydrophillic porous members which are only activated when disc 103 spins in one direction (due to the Coriolis effect's influence on in-disc forces and pressures) or active valves controlled by a mechanical or electrical actuation. In on one embodiment the valve can be a siphon valve where a change in rotational speed of the disc activates the valve. Further, other valves can be used in disc 103 include, but are not limited to are one-time control valves that can use placement of bubble in channel to prevent flow and/or can use a polymer that swells with water contact to directly close off a channel, to indirectly close off channel through membrane to avoid possibility of contamination, or to indirectly or directly close off a channel after sample has left area by separating a small volume of sample for this purpose. Further, some embodiments of disc 103 employ active components, such as general valves or onsite pumps for fluid control within disc 103.

Figure 5:
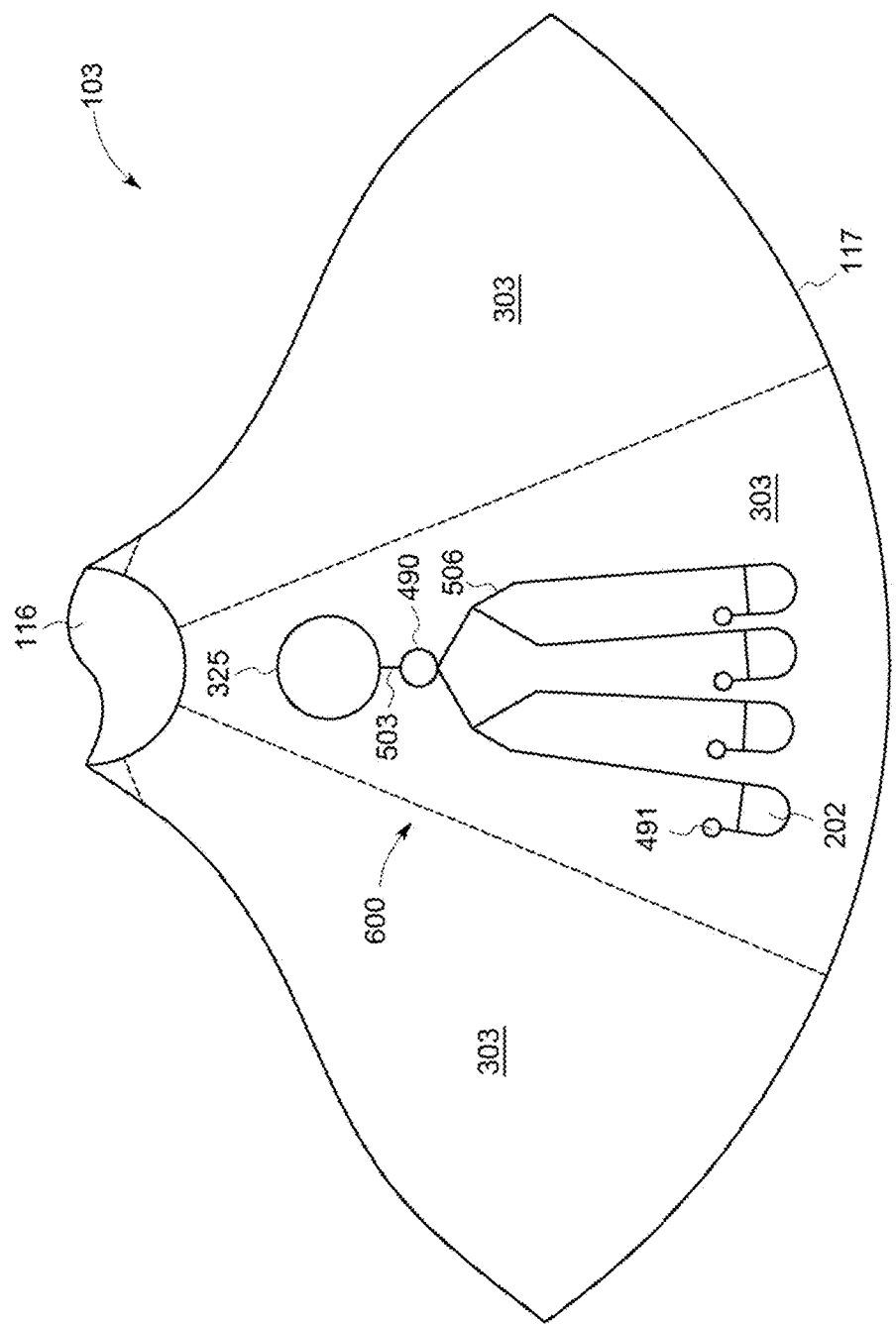
FIG. 5 is an exemplary embodiment of a microfluidic disc.

FIG. 5 depicts a fluidics network diagram for an embodiment of disc 103 that uses burst valves for control of a fluidics network 600. Disc 103, has fluidics networks 600 in each radial testing area 303, arranged around hub 116. For simplicity purposes, a fluidics network is only shown in one radial testing area 303. The sample or reagent is added to reservoir 325, for each testing area 303. A reservoir outlet channel 503 may terminate in a first valve 490 at its downstream end. First valve 490 is located at the intersection of reservoir outlet channel 503 and distribution network 506. Reservoir outlet channel 503 provides a path for the fluid to flow from reservoir 325 to distribution network 506. First valve 490 can be any valve that selectively allows the fluid of reservoir 325 to be transferred to distribution network 506. Distribution network 506 is a network of channels that delivers the contents of reservoir 325 to a series of optical chambers 202 in radial testing area 303.

In one embodiment, first valve 490 is a burst valve designed using the surface energies of the materials on the reservoir channel surface and the diameter and geometry of the channel to stop fluid from flowing until disc 103 is spun at a sufficient velocity to overcome the burst valve. This prevents the fluid from flowing into the optical chambers 202 at an uncontrolled and unknown time, thereby starting the reaction before the reaction can be monitored and accurately timed. In yet another embodiment, the valve may be a siphon valve.

In another embodiment, the first valve 490 can be formed as a passive valve generated by hydrophobic surface treatment utilizing plasma etching which manipulates the surface with wettability gradients adapted for microfluidic systems, as described in "Smart" Polymeric Microfluidics Fabricated by Plasma Processing: Controlled Wetting, Capillary Filling and Hydrophobic Valving, Katerina Tsougeni, et al. (Nov. 30, 2009), for example. It should be understood by one of ordinary skill in the art that the first valve 490 can be formed by surface treating the channel between the reservoir outlet channel 503 and distribution network 506 or by a physical barrier or membrane positioned within the passageway. In yet another embodiment, the first valve 490 is a mechanical valve that can be selectively actuated manually, electrically, or by way of pressure differential thereacross to allow fluid to flow between the reservoir outlet channel 503 and distribution network 506. In still a further embodiment, the first valve 490 is a membrane positioned within the passageway between the reservoir outlet channel 503 and distribution network 506.

Disc 103 is spun at a sufficient rotational speed to move fluid through fluidics. More specifically, move fluid from reservoir 325 through reservoir outlet channel 503, past first valve 490, into distribution network 506, which directs fluid into four optical chambers 202 near the outer edge 117 of disc 103, where the reaction takes place. A vent tube 507 with a relatively-high-pressure second valve 491 allows the venting of air from the optical chamber 202, while preventing the sample from flowing out of optical chamber 202, thereby retaining the sample within disc 103. In some embodiments, second valve 491 is a burst valve. It is contemplated that in other embodiments, second valve 491 can be a hydrophobic membrane and also be used to prevent the sample from flowing out of optical chamber 202 through vent tube 507. Further, in other embodiments, second valves 491 can be a mechanical valve, membranes, insert or film positioned within the passageway, or formed from surface treatment of vent tube 507. Each second valve 491 can be manually or electrically actuated or can be actuated due to a pressure differential thereacross.

Exemplary embodiments of a second valve 491 may be a burst valve, a passive valve generated by hydrophobic surface treatment utilizing plasma etching, a hydrophobic porous membrane, a mechanical valve, or any other type of valve sufficient to allow air to escape from optical chamber 202, while preventing the sample from flowing out of optical chamber 202, thereby retaining the sample within disc 103. In this embodiment, the reagents and standards are immobilized in optical chamber 202 by drying on the surface of optical chamber 202. The Coriolis effect can be used to actively swirl and mix the contents of optical chamber 202, which solvates the contents and brings them into solution to react. Alternately, the inertia of the fluid can aid in inducing the swirling by changing the speed or reversing the rotation. Any excess fluid is simply stored in the distribution network 506 and because of limited diffusion (the molecules in question are large and move very slowly by diffusion) do not take part in these reactions. In this way the sample volume, which is critical to accurate results, is controlled and dictated by the volume of optical chamber 202. As can be seen, optical chambers 202 also act as reaction chambers. The reactions taking place within optical chambers 202 are monitored optically. In some embodiments, the optical monitoring is performed using blue light at about 405 nm. However, it is contemplated that a person having ordinary skill in the art can choose to use a different wavelength of light.

Multiple drying processes are suitable for immobilizing standards and reagents within optical chamber 202 including, but not limited to, a vacuum drying process at ambient temperature or a freeze drying process (lyophilization). In yet another embodiment, the standards and reagents may be dried at ambient temperature or freeze dried. In some embodiments, the material (standards and reagents) does not need to be totally dried, especially if non-aqueous solvents are used, but by partial drying or other method left in or changed to a state where it can be physically immobilized.

In FIG. 5, reservoir portion is comprised of reservoir 325. Further, distribution network portion 625 is comprised of first valve 490 and distribution network 506. Metering portion is comprised of distribution network 506 and optical chamber portion 635. Further, optical chamber portion 635 is comprised of optical chamber 202. It is contemplated that there are many other fluidic schemes which differ from that of FIG. 5.

Figure 6:
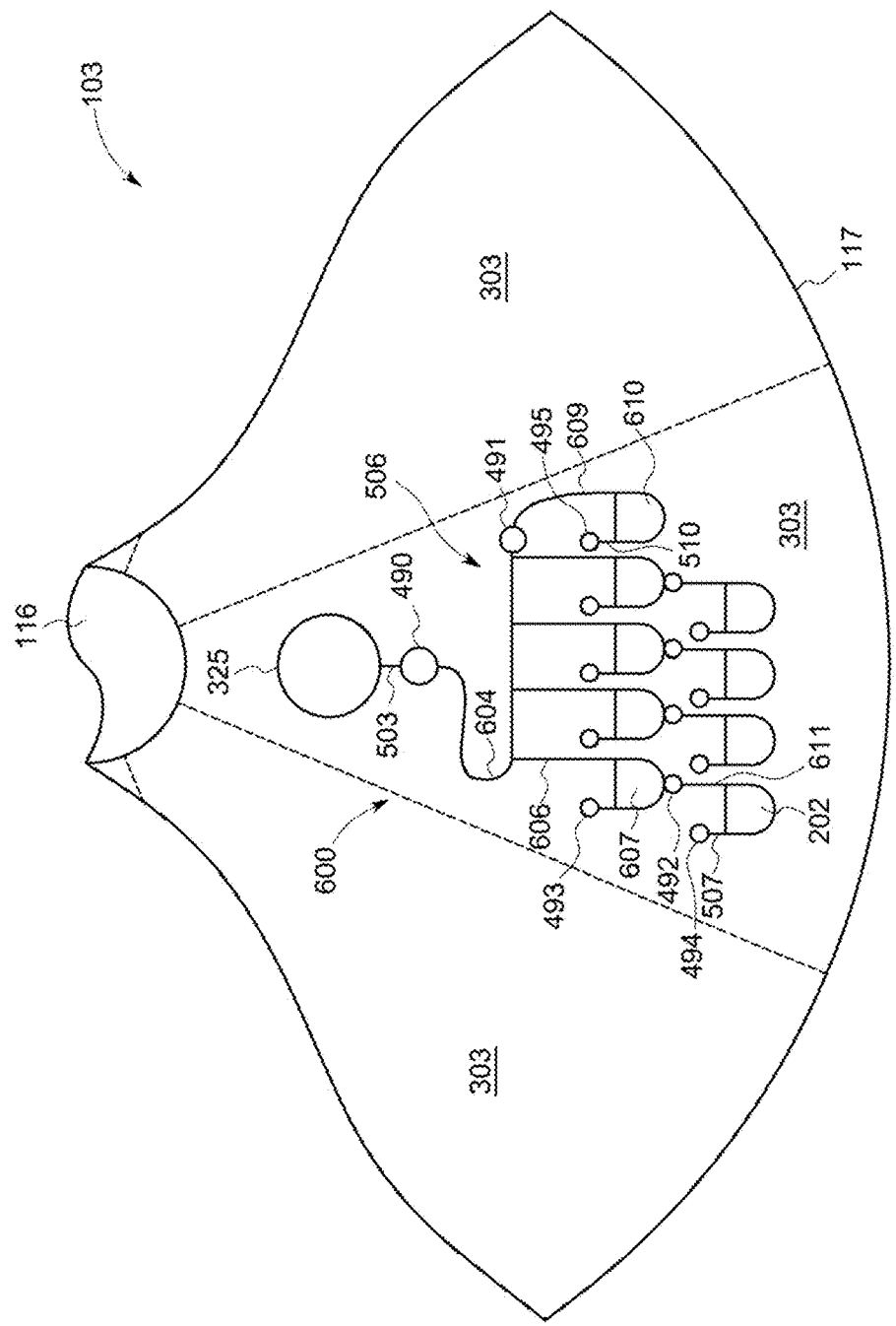
FIG. 6 is an exemplary embodiment of a microfluidic disc.

Sometimes different reagents or parts of reagents need to be stored or mixed separately for better performance or shelf life. For example, if the endotoxin standards are mixed with the sample before mixing with reagent, the response would more closely match sample endotoxin, increasing accuracy. Other times, liquid reagent may need to be used instead of dried or otherwise immobilized material. One embodiment which that addresses this scenario is shown in FIG. 6.

Many approaches to the test reagent and standards deposition may be used to reduce mixing time, bubble formation, resolubilization time, ease of manufacturing, and detection sensitivity. The approaches may encompass both chemical and physical means to produce the desired results. Chemical means may include the use of chemical additives. Examples of chemical additives include solubility enhancing agents, such as the saccharides sucrose, glucose, lactose, and mannitol, as well as anti-flaking agents, such as aqueous polymer solutions comprising poly(ethylene oxide), polyethylene glycol, polyvinyl alcohol, hydroxypropyl cellulose, or hydroxypropyl methyl cellulose. Physical means may include various coating, spraying, or drying techniques during the deposition process.

In some embodiments, an endotoxin detection reagent may be deposited in every optical chamber 202. Alternatively, there is no endotoxin detection reagent in any of the optical chambers, allowing the user to add endotoxin detection reagents from a preferred supplier either as Control Standard Endotoxin (CSE) which is match to LAL reagent lots, or Reference Standard Endotoxin (RSE) which is a universal reference and has the same titer regardless of the LAL reagent used. In one embodiment, the endotoxin detection reagent may be amoebocyte lysate. The use of the natural absorption of LAL, or the addition of turbidimetric or chromogenic non-LAL reactive tracers, such as optical dye, to the LAL and endotoxin may also be used to reduce testing errors. A tracer is an inert compound that is added to a fluid to aid in determining the volume, fluid location and movement (fluid motions). The tracer may also be used to aid in validating the measurement data. Suitable tracers include, but are not limited to, dyes.

The endotoxin standard may be deposited in only a portion of the optical chambers 202. In addition, the endotoxin standard may be deposited in various concentrations from optical chamber 202 to optical chamber 202. The optical chambers 202 may be preloaded or predeposited with endotoxin standards, wherein the endotoxin concentrations vary from optical chamber 202 to optical chamber 202, such that the user merely has to add the sample to be tested to the reservoirs 325. In one embodiment, the endotoxin detection reagent and endotoxin standard may be deposited in the optical chambers 202 such that all of the tests and replicates required by USP 85 may be performed simply by adding the samples to reservoirs 325. In such an embodiment, each optical chamber 202 comprises either a separate given test, or a replicate of a given test.

In one embodiment, the lowest concentration may be confirmed in four replicates, wherein four (4) of the ninety-six (96) optical chambers 202 each comprise one replicate. Alternatively, the optical chambers 202 may be preloaded with endotoxin standards such that the inhibition/enhancement tests (or "spikes"), including replicates, may be performed. Alternatively, the optical chambers 202 may be preloaded such that the quantitative tests, wherein the concentration of bacterial endotoxins in a given sample is quantified, may be performed. In yet another embodiment, the optical chambers may be preloaded such that all the tests and replicates required under USP 85, including the lysate sensitivity, the inhibition/enhancement, and quantitative tests, may be performed on the same disc 103.

The test reagents and standards may be mixed with chemical additives before deposition, such as solubility enhancing agents and anti-flaking agents. The reagents and standards are deposited within disc 103 without interfering with the optical windows 205 or optical bench 107, thereby allowing an initial sample absorption measurement. In one embodiment, the disc 103 may be covered with a seal means that prevents the passage of water and oxygen, whereby disc 103 and its contents may be kept dry to a humidity level less than about 5%.

Fluid motivation within disc 103 may be provided by centripetal force, which is determined by the position of the fluid within disc 103 and rotational speed of disc 103. Fluid motivation by centripetal force can be accurately and repeatably controlled by reader 100, and allows for such things as reversing rotational direction or rotational speed of disc 103 to change the flow of the sample through disc 103.

As can be seen, disc 103 in FIG. 6 resembles disc 103 in FIG. 5, except the fluidics network 600 in each radial testing area 303 is different. For convenience, only a fluidics network 600 is shown in only one radial testing area 303, however it is understood that a fluidics network 600 is present in each radial testing area 303. Reservoir 325 receives the sample and first valve 490 is at the downstream end of reservoir outlet channel 503. First valve 490 is at the upstream end of main distribution channel 604 and second valve 491 is at the downstream end of main distribution channel 604. The upstream end of four (4) aliquoting inlet channels 606 intersect with and receive sample fluid from main distribution channel 604. Each aliquoting inlet channel 606 delivers sample fluid to an aliquoting chamber 607. Further, each aliquoting chamber 607 has a fourth valve 493 or hydrophobic membrane at the end of aliquoting chamber vent tube 508. Third valve 492 is located at the downstream end of aliquoting chamber 607. The upstream end of optical chamber inlet channel 611 receives sample fluid through third valve 492 and delivers fluid to optical chamber 202 for testing. The upstream end of waste chamber inlet channel 609 receives waste fluid through second valve 491 and delivers waste fluid downstream to waste fluid chamber 610. Further, waste fluid chamber 610 has a sixth valve 495 or hydrophobic membrane at the end of waste chamber vent tube 510.

In operation, first valve 490 prevents premature flow of the sample through distribution network 506. First valve 490, second valve 491, and third valve 492 are designed to operate at different pressures, increasing as the fluid moved downstream so that when it clears one it valve, it only moves to the next valve but not beyond. In this case the pressure needed to move through first valve 490 is less than that needed for the second valve 491 which are both less than that needed to go through the third valve 492 at the head of optical chamber inlet channel 611 leading to optical chamber 202. Each optical chamber 202 also has a fifth valve 494 or hydrophobic membrane at the end of its vent tube 507, to prevent the loss of fluid from optical chamber 202 through vent tube 507.

Once disc 103 starts to spin at a sufficient rate, fluid moves from reservoir 325 down reservoir outlet channel 503 and through first valve 490 down main distribution channel 604 to aliquoting inlet channels 606, which distributes the fluid to aliquoting chambers 607. These chambers can be for volume measurement only, or they can also have reagent (such as Endotoxin standard) isolated in them to mix in aliquoting chamber 607 or later downstream in optical chamber 202 using the Coriolis effect as detailed before. Fluid will not travel past second valve 491 or third valve 492 until the speed of the rotation of disc 103 is sufficient to generate enough pressure to move second valve 491 or third valve 492. Once disc 103 is spun at a velocity that allows fluid to flow past second valve 491, but not third valve 492, excess fluid will be drained away from aliquoting chambers 607 and into waste fluid chamber 610, thereby drawing air into distribution network 506. The disc 103 is then spun even faster, at a velocity that allows fluid to flow past third valve 492, and an accurate volume of sample fluid from aliquoting chamber 607 flows downstream into optical chamber 202, perhaps with reagent also mixed in that was present in aliquoting chamber 607. A reaction will then take place and be monitored in optical chambers 202.

One reason the sample fluid may need to be metered via aliquoting before the sample fluid is moved into optical chamber 202, is if the LAL reagent is delivered to disc 103 as a liquid at the time of the actual analysis instead of being immobilized disc 103. Using an LAL liquid reagent involves moving and precisely metering both the sample fluid and reagent within disc 103. This could be done by adding a second layer to disc 103 depicted in FIG. 6. In one embodiment, this second layer would contain a parallel fluidics path for LAL reagent that is similar or identical to the fluidics path described above for use with the sample fluid. The two parallel paths on separate layers would meet at optical chamber 202, which is shared by the two fluid systems. Accordingly, the sample fluid system will deliver sample fluid to optical chamber 202 and the reagent system will deliver the LAL reagent to optical chamber 202. Both would have channels leading to optical chamber 202 and partially fill optical chamber 202 when the pressure of third valve 492 is exceeded by disc 103 achieving a sufficient rotational velocity. These two fluids would then be mixed together in optical chamber 202 and the resulting reaction monitored.

In some embodiments, first valve 490, second valve 491, and third valve 492 can be mechanical valves, membranes, inserts or films positioned within the channel, or formed from surface treatment of the channel. First valve 490, second valve 491, and third valve 492 can be manually or electrically actuated or can be actuated due to a pressure differential thereacross. Exemplary embodiments of any of the first valve 490, second valve 491, and third valve 492 may be a burst valve, a passive valve generated by hydrophobic surface treatment utilizing plasma etching, a mechanical valve, or the like.

In some embodiments, fourth valve 493, fifth valve 494, and sixth valve 495 are burst valves. It is contemplated that in other embodiments, fourth valve 493, fifth valve 494, and sixth valve 495 can be a hydrophobic membrane and also be used to prevent the sample from flowing out of their respective chambers through the vent tubes. Further, in other embodiments, fourth valve 493, fifth valve 494, and sixth valve 495 can be mechanical valves, membranes, inserts or films positioned within the vent tube, or formed from surface treatment applied to the vent tube. Fourth valve 493, fifth valve 494, and sixth valve 495 can be manually or electrically actuated or can be actuated due to a pressure differential thereacross. Exemplary embodiments of fourth valve 493, fifth valve 494, and sixth valve 495 may be a burst valve, a passive valve generated by hydrophobic surface treatment utilizing plasma etching, a hydrophobic porous membrane, a mechanical valve, or any other type of valve sufficient to allow air to escape from their respective chambers, while preventing the sample fluid from flowing out of the vent tube, thereby retaining the sample within disc 103.

Even though only the left most aliquoting inlet channel 606, aliquoting chamber, optical chamber inlet channel 611, optical chamber 202, and third valve 494 are discussed in conjunction with FIG. 6, it is understood that the three corresponding groups of structures to the right have the same function.

In FIG. 6, reservoir portion 620 is comprised of reservoir 325 and reservoir outlet channel 503. Distribution network portion 625 is comprised of first valve 490 and main distribution channel 604. Metering portion 630 is comprised of aliquoting inlet channel 606, aliquoting chamber 607, second valve 491, and third valve 492. Optical chamber portion 635 is comprised of optical chamber inlet channel 611 and optical chamber 202.

Figure 8:
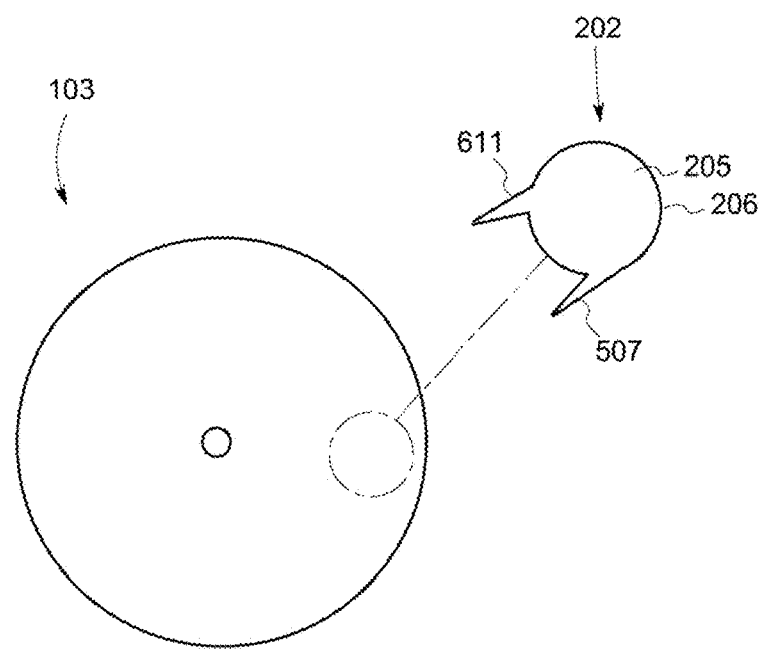
FIG. 8 is an exemplary embodiment of an optical chamber.

Turning to FIG. 8, disc 103 is shown with an embodiment of optical chamber 202 having an inlet 611, vent 507, sidewall 206, and optical windows on the top side and bottom side of disc 103. In some embodiments, sidewall 206 has a generally circular shape around the entirety of optical chamber 202. However, in other embodiments, the hub side of sidewall 206 between inlet and vent 507 is straight and the remainder of sidewall 206 is generally "U" shaped.

Figure 9A:
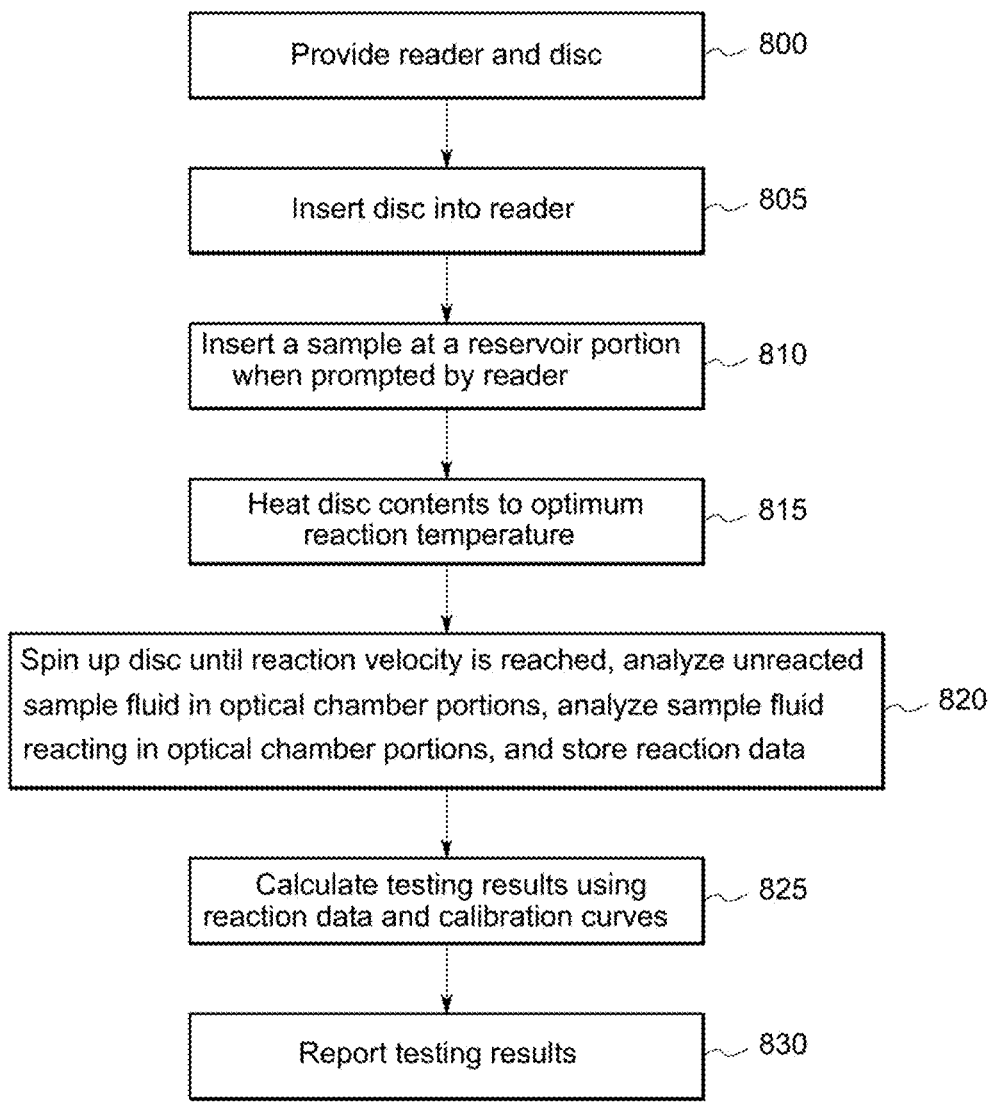
FIGS. 9A, 9B, and 9C are exemplary embodiments of testing processes or methods using a reader and a microfluidic disc.

An exemplary testing process or method using reader 100 and disc 103 is shown in FIG. 9A. In step 800, a user provides a disc, reader, and samples to be tested. In step 805, the user inserts disc 103 into reader 100. Information from disc 103, such as lot, range, or expiration date, can be transferred to the reader either manually or automatically from markings or information stored within the disc. Reader 100 rotates disc 103 in step is rotated in step 815 such that a reservoir portion 620 is lined up with an inlet or port in the lid 102 of reader 100, which only allows the user to insert a sample into the correct reservoir portion 620 of disc 103. The user is prompted and instructed via user interface 113 as to what sample to insert. In some embodiments that use liquid reagents, CPU will also line up an inlet or port in the lid 102 with reservoir portion 620 and prompt and instruct the user via user interface 113 as to what reagent to insert into reservoir portion 620.

In step 815, the disc contents are heated to optimum reaction temperature within enclosure 101 of reader 100. CPU 118 achieves and maintains the optimum reaction temperature using a heater and thermometer. Once all of the samples and reagents are loaded into reservoir portions 620 of disc 103 and the enclosure 101 is at optimum reaction temperature, in step 802, CPU 118 instructs the centripetal disc drive 115 to spin disc 103 until reaction velocity is reached. The sample fluid is analyzed in the optical chamber portions 635 before the fluid reacts with reagents in optical chamber portions 635, and the sample fluid is analyzed while reacting in optical chamber portions 635. The analysis information collected in this step, also known as reaction data, is stored in memory 119.

Once the reaction data is stored in memory 119, in step 825, CPU retrieves the reaction data, uses the reaction data to create calibration curves, and then uses the reaction data and calibration curves to calculate testing results. The testing results are reported to the user in step 830 via user interface 113.

Figure 9B:
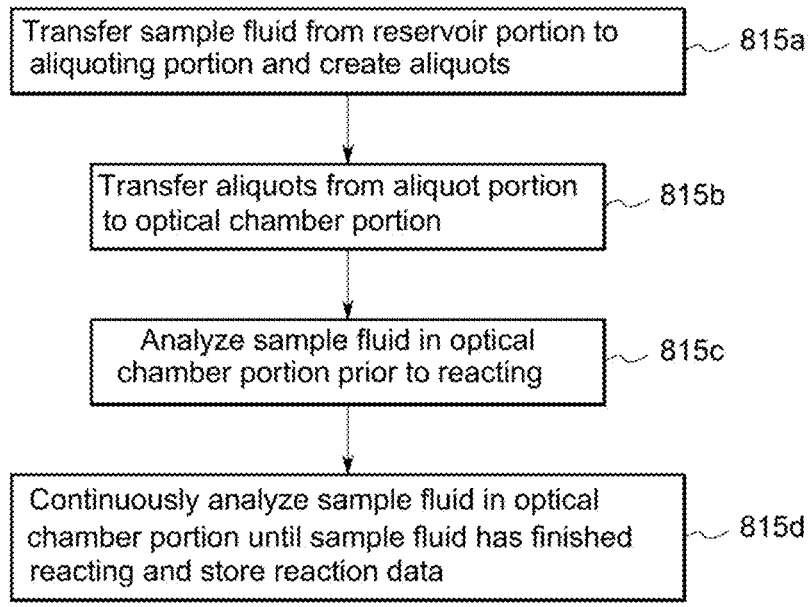
Figure 9C:
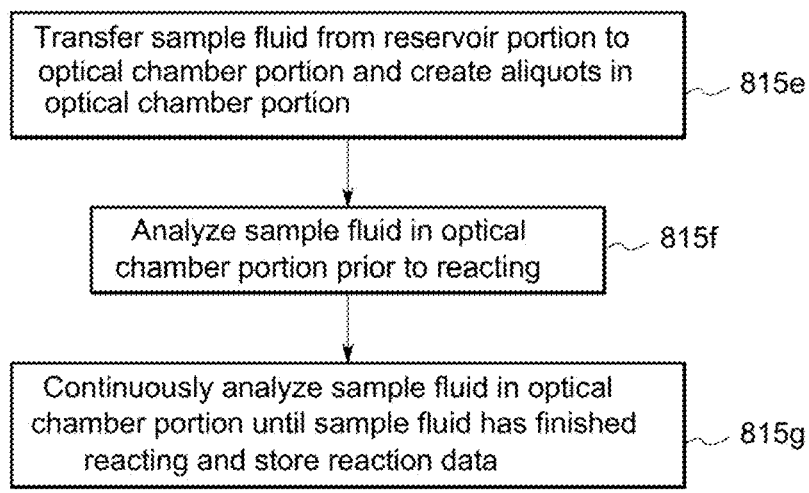

FIGS. 9B and 9C expound upon step 820 in FIG. 9A. FIG. 9B details the actions that take place in step 820 in an embodiment of the method of FIG. 9A. In step 815*a*, sample fluid is transferred from reservoir portion to metering portion and aliquots are created. This can be done by spinning disc 103 at a sufficient velocity such that the sample fluid flows from reservoir portion 620 and across a valve into metering portion 630. In some embodiments of disc 103, a waste fluid chamber 610 is present and once spinning disc 103 reaches a sufficient velocity the remaining fluid from reservoir portion 620 and distribution network portion 625 flows across a valve and into waste fluid chamber 610.

In step 815*b*, after the aliquots of sample fluid are created the aliquots are transferred from aliquot portion 630 to optical chamber portion 635. This can be done by spinning disc 103 at a sufficient velocity such that the aliquots of sample fluid flows across a valve from the metering portion 630 into the optical chamber portion 635.

In step 815*c*, once a portion of the sample fluid is in optical chamber portion 635 the sample fluid is analyzed using photospectrometry or any other optical measuring process prior to the fluid contacting and/or reacting with any reagent within optical chamber portion 635. In step 815*d*, the sample fluid is continuously analyzed in optical chamber portion 635 until entire aliquot of sample fluid has finished reacting in each optical chamber portion and the reaction data is stored.

FIG. 9C details the actions that take place in step 820 in an embodiment of the method of FIG. 9A. In step 815*e*, sample fluid is transferred from reservoir portion 620 to optical chamber portion 635 via distribution network portion 625. This can be done by spinning disc 103 at a sufficient velocity such that the sample fluid flows from reservoir portion 620 into optical chamber portion 635. In some embodiments, a valve is present between reservoir portion 620 and optical chamber portion 635.

Once a portion of the sample fluid is in optical chamber portion 635, in step 815*f*, the sample is analyzed using photospectrometry or any other optical measuring process prior to the fluid contacting and/or reacting with any reagent within optical chamber portion 635. The sample fluid is then continuously analyzed in optical chamber portion 635 until sample fluid has finished reacting in each optical chamber portion 635 and the reaction data is stored.

Turning back to disc 103, depicted in FIGS. 3 and 5-7, in some embodiments of disc 103, LAL reagent is immobilized (e.g. dried) within optical chambers 202, and is mixed with the sample fluid using the circulation the Coriolis effect will have on the fluids in optical chamber 202. It is also possible to increase this mixing within optical chamber 202 by using the inertia of the fluid within optical chamber 202 and "shaking" the fluid the fluid within optical chamber 202 back and forth by changing the rotational speed or reversing rotational direction of disc 103.

In some embodiments of optical chamber 202, the aggressiveness of mixing within optical chamber 202 can be enhanced by one or both of intentional entrainment of bubbles within optical chamber 202 or addition of beads into optical chamber 202 (which can be magnetic and moved as the spinning disc goes past a fixed magnet). In some embodiments, the beads within optical chamber 202 are comprised of a material that is attracted to magnets (e.g. ferromagnetic or ferrimagnetic material), thereby the beads will be agitated as they move past a magnet fixed within reader 100. Mixing can be enhanced with fluid motion in and out of the optical chamber, such as reciprocal flows between chambers through an orifice or channel. Not only does this mix the fluids transferred by diffusion in any channels or turbulence in open areas, the transfer chaotically interferes with the Coriolis swirling increasing its mixing efficiency.

As can be seen, the mixing within optical chamber 202 can be done using the Coriolis effect and can be very active and energetic, which helps for mixing large molecules that diffuse slowly, with molecules that aggregate, and with molecules that stick to surfaces.

In some embodiments of disc 103, the optical chamber 202 may be wide or thick, thereby forming a longer optical path leading to more sensitivity. It is contemplated that in some embodiments of disc 103, the optical path length is matched to sensitivity requirements.

In additional embodiments of disc 103, mixing is performed in mixing chambers located upstream from optical chambers 202. It is contemplated that optical chambers 202 and mixing chambers, if present, can be optimized for thicker sections (e.g., longer optical path lengths) and/or optimized for mixing with reagents immobilized on interior surfaces. In one embodiment, the reagents may be immobilized on windows or on sidewalls 206. Thicker optical chambers 202 and mixing chambers allow for alternate immobilizations designs, such as allowing for the use of powdered reagents.

In further embodiments, the flow pattern in optical chamber 202 may also be modified, e.g., to have more flow velocity over surfaces where reagents are immobilized, by changing the geometry of the optical chamber 202. In one embodiment, the sidewalls 206 of optical chamber 202 could be angled such that the fluid flow constructed by the sidewalls 206 could be angled so that the fluid flow constricted by sidewalls 206 is moved in a different or transverse direction than the fluid's normal circulation direction in optical chamber 202. In additional embodiments of optical chamber 202, vanes, channels, or voids in optical chamber 202 could also be used to move fluid counter to its normal circulation and increase the effectiveness of mixing in optical chamber 202. In further embodiments, the geometry of sidewalls 206 promotes flow paths that effectively mix material close to the surface of sidewalls 206.

The optical chamber 202 is configured to allow the fluid to be analyzed and monitored optically using spectrophotometry when at least a portion of the fluid is positioned within the optical chamber 202. The optical chamber 202 is configured to allow for accurate optical density measurement and can also be used to immobilize reagents immobilization or as a mixing chamber for the fluid. The optical chamber 202 provides the ability to monitor optical density of the fluid at all phases of analysis including: (1) before addition of or mixing with reagent(s) so as to get material and reader baseline data; (2) after addition or mixing of reagent but before reagent solvation to get fluid baseline data; and (3) continuous monitoring of the fluid during analysis and testing process. After the addition or mixing of reagent but before reagent solvation, the optical chamber 202 can be used to analyze for fluid present therewithin due to changes in optical reflection from surfaces of the optical chamber 202. This can be done to provide a starting point to improve accuracy of timing of subsequent optical measurements. The optical chamber 202 can be used to verify or check for correct amount of reagent by using natural absorption at normal optical monitoring wavelengths, use tracers at normal optical monitoring wavelengths, use natural absorption at alternate optical monitoring wavelengths, and/or use tracers at alternate optical monitoring wavelengths. Continuous monitoring of the fluid within the optical chamber 202 can be done on a much more frequent basis than standard multi-use plate readers to provide improved time resolution, better noise rejection, and greater ability to accurately extrapolate to an endpoint for the data. The extrapolation can be performed using curve fitting techniques, such as regression methods, weighted least-squares methods, data transformation methods, and parametric and non parametric methods. Continuous monitoring of the fluid within the optical chamber 202 can also be done with fixed optics in reader 100.

In one aspect of the invention, a microfluidic disc for use with a centripetal microfluidics system is disclosed. The microfluidic disc may comprise at least two testing areas wherein each testing area includes a reservoir portion for receiving at least one fluid sample. The reservoir portion may comprise a reservoir and a reservoir outlet. The disc may comprise a distribution network portion in fluid communication with the reservoir portion. Each distribution network portion may comprise a distribution network of at least four (4) testing channels, wherein each testing channel has a metering portion and at least one analysis chamber portion. The analysis chamber portion may comprise a mixing chamber for mixing samples and reagents and an optical chamber portion that is compatible with an optical reader. The mixing chamber and the optical chamber portion may be separate, integral with each other, or the same chamber that serves both a mixing function and an optical chamber function. The metering portion may be sized to meter an aliquot of the fluid sample for analysis in the analysis chamber portion. At least one testing channel portion has at least one reagent isolated therein. The reagent may comprise a LAL-reactive substance.

In another embodiment of the disc, at least one distribution network is a calibration network comprising at least eight (8) testing channels. At least two (2) of the channels have no LAL-reactive substance therein. At least two (2) of the channels have a first amount of a LAL-reactive substance isolated therein. At least two (2) of said channels have a second amount of a LAL-reactive substance isolated therein, and at least two (2) of the channels have a third amount of a LAL-reactive substance isolated therein.

In yet another embodiment of the disc, at least one distribution network is a sample measurement network comprising at least four (4) testing channels. At least two (2) of the channels have no LAL-reactive substance therein and at least two (2) of the channels have a spike with a fourth amount of a LAL-reactive substance isolated therein. In another embodiment, the first, second, third amounts may be the same or different. If endotoxin is used, the first amount may be chosen such that when the endotoxin is in a solution, the concentration ranges from 0.005 to 0.5 EU/mL. Similarly, the second amount may range from 0.05 to 5.0 EU/mL and the third amount may range from 0.5 to 50 EU/mL.

In another embodiment of the microfluidic disc, at least one valve may be positioned between a) the reservoir portion and the distribution network portion and/or b) the metering portion and the analysis chamber portion. The valve may be configured to allow centrifugal forces to motivate the aliquot to flow across the valve from the metering portion to the analysis chamber portion.

In yet another embodiment, all of the analysis chamber portions may comprise mixing chamber and an optical chamber. The mixing chamber may have at least one additional reagent isolated therein. The additional reagent may comprise a detection reagent. The mixing chamber may have thick sidewalls optimized for mixing the detection reagent immobilized on the sidewalls with the aliquot. The thick sidewalls may promote flow paths that mix the reagents and the aliquot close to the thick sidewalls. In another embodiment, the analysis chamber may be configured to enable mixing the aliquot with the reagent using at least one of the Coriolis effect, inertial effect, or bubbles and/or beads entrained therein.

In yet another embodiment, the distribution network portion may further comprise a main distribution channel, a waste inlet channel, and a waste chamber for confining any excess fluid sample and separating the excess from the aliquot. In another embodiment, the disc may be configured to allow centrifugal forces to eliminate bubbles from the sample fluid in the optical chamber portion.

In another embodiment, a reader configured to test fluid samples in a microfluidic disc is disclosed. The reader may comprise an enclosure, an optical bench, a centripetal disc drive, and a controller. The microfluidic disc may comprise at least two testing areas wherein each testing area includes a reservoir portion for receiving at least one fluid sample. The reservoir portion may comprise a reservoir and a reservoir outlet. The disc may comprise a distribution network portion in fluid communication with the reservoir portion. Each distribution network portion may comprise a distribution network of at least four (4) channels, wherein each channel has a metering portion and at least one analysis chamber portion. The metering portion may be sized to meter an aliquot of the fluid sample for analysis in the analysis chamber portion.

In another aspect of the reader and microfluidic disc, the sensing method is any of a variety of optical measurements, including transmission, absorption, optical density, color, color value, hue, spectrum, turbidity, scattered light, chemiluminescence, and fluorescence. In another aspect of the reader and microfluidic disc, the sensing method is method capable of sensing changes in the fluid remotely in a spinning disc, including more-complex optical methods such as Raman spectroscopy, nuclear magnetic resonance, and surface plasmon resonance, and non-optical methods such as electrical capacitance, magnetism, sonic resistance, and sonic refraction.

In another aspect, the enclosure may include an inlet for inserting a fluid sample into a reservoir of the disc. The inlet and reader may be configured to prevent the user from inserting the fluid sample into an incorrect reservoir.

In yet another embodiment of the reader, at least one distribution network may be a calibration network comprising at least eight (8) testing channels. At least two (2) of the channels have no LAL-reactive substance therein. At least two (2) of the channels have a first amount of a LAL-reactive substance isolated therein. At least two (2) of the channels have a second amount of a LAL-reactive substance isolated therein, and at least two (2) of the channels have a third amount of a LAL-reactive substance isolated therein.

In another aspect of the reader, at least one distribution network may be a sample measurement network comprising at least four (4) testing channels. At least two (2) of the channels have no LAL-reactive substance therein, and at least two (2) of the channels have a spike with a fourth amount of a LAL-reactive substance isolated therein.

In yet another embodiment of the invention, a method for testing at least one fluid sample for LAL-reactive substances is disclosed. The method may comprise inserting a microfluidic disc into a optical reader. The microfluidic disc may comprise at least two testing areas wherein each testing area includes a reservoir portion for receiving at least one fluid sample. The reservoir portion may comprise a reservoir and a reservoir outlet. The disc may also comprise a distribution network portion in fluid communication with the reservoir portion. Each distribution network portion may comprise a distribution network of at least four (4) testing channels, wherein each testing channel has a metering portion and at least one analysis chamber portion comprising an optical chamber. The metering portion may be sized to meter an aliquot of the fluid sample for analysis in the optical chamber.

The reader may comprise an enclosure, an optical bench, a centripetal disc drive, an inlet for introducing said fluid sample into said disc, and a controller. A fluid sample is inserted into the inlet of the reader. The reader spins the disc until a reaction velocity is reached. The reader analyzes the aliquot in the optical chamber using the optical bench to obtain measurement data and/or reaction data. The measurement data and/or reaction data and calibration curves may be used to calculate testing results. The reader may then report and/or store the test results.

In another embodiment, at least one reagent comprising a detection reagent and/or LAL-reactive substance may be introduced into the reader inlet. The reader may spin the disc until reaction velocity is reached. The aliquot is allowed to react with the detection reagent. The aliquot may be analyzed in the optical chamber using the optical bench to obtain measurement data and/or reaction data. The measurement data and/or reaction data and calibration curves may be used to calculate testing results. The reader may then report and/or store the test results.

In another method embodiment, at least one optical chamber has at least one reagent isolated therein. The reagent may comprise a LAL-reactive substance and/or a detection reagent. In yet another embodiment, the method may further comprise transferring the fluid sample from the reservoir to the metering portion and metering said aliquot. The aliquot may be transferred from the metering portion to the optical chamber. The aliquot may be continuously monitored in the optical chamber to obtain measurement data and/or reaction data using the optical bench until the aliquot has finished reacting. The measurement data and/or reaction data and calibration curves may be used to calculate testing results. The reader may then report and/or store the test results.

In another method embodiment, the measurement data and/or reaction data may comprise aliquot volumes, reaction kinetics, fluid motions, transmission, absorption, optical density, color, color value, hue, spectrum, turbidity, scattered light, chemiluminescence, fluorescence, and magnetic resonance. The method and/or said measurement data and/or reaction data may be validated using historical measurement data and/or data from known reaction kinetics. In yet another embodiment, a tracer may be immobilized within the analysis chamber to aid in measuring and validating the aliquot volume.

EXAMPLE

The following example demonstrates an embodiment wherein endotoxin standards are preloaded into disc 103. The endotoxin standard range is shown in Table 1. The endotoxin standard range, however, may be different in other embodiments.

TABLE 1

| Range (EU/mL) | Lowest (EU/mL) | Mid Range (EU/mL) | Highest (EU/mL) |
|---|---|---|---|
| 0.005-0.5 | 0.005 | 0.05 | 0.5 |
| 0.01-1 | 0.01 | 0.1 | 1 |
| 0.05-5 | 0.05 | 0.5 | 5 |
| 0.1-10 | 0.1 | 1 | 10 |
| 0.5-50 | 0.5 | 5 | 50 |

As explained above, an exemplary embodiment of disc includes twenty-four (24) testing areas 303 formed therein, wherein each testing area 303 is configured to test a separate fluid. Table 2 illustrates the reagent within each optical chamber 202 of a disc 103 having twenty-four (24) testing areas 303, wherein each testing area includes four (4) optical chambers 202.

FIG. 5 illustrates another embodiment of the reagent within each optical chamber 202 of a disc 103 having twenty-four (24) testing areas 303, wherein each testing area 303 includes four (4) optical chambers 202. Table 1 indicates that the lowest, mid-range, and highest endotoxin levels depend on the range of the particular disc 103, wherein the range level within a disc 103 is the same for each testing area 303. The units of the different ranges are in EU/mL (Endotoxin Units per milliliter). Calibration replicates are averaged to generate a calibration curve. A negative control must be statistically different than the lowest calibration level. Sample analysis replicates are averaged for each reported value. Positive control spikes are averaged and the difference between spiked analysis and base analysis must be within 50% and 200% of the mid-range value for a valid analysis. The calibration curve for each disc 103 shown in Tables 2 and 3 is based upon a triple replicate control. Table 1 is for a disc 103 in which each testing area 303 has a reservoir 325 containing either sample fluid to be tested or LAL Reagent Water that is delivered to four (4) optical chambers 202 in the testing area 303. Table 2 is for a disc 103 in which the four (4) optical chambers 202 of four (4) testing areas 303 are provided with LAL Reagent Water from one (1) shared reservoir 325.

Each disc 103 contains at least one sample fluid, which itself consists of at least two replicates of a standard analysis and two positive controls, i.e. spiked with Endotoxin; and a calibration curve formed with at least 3 points and negative controls (blanks), each with at least 2 (or 3) replicates.

TABLE 2

| Sample Reservoir | Sample | Optical Chamber | Endotoxin Standard | Description |
|---|---|---|---|---|
| 1 | LAL Reagent Water | 1 | 0 | Negative Control (Blank) Rep 1 |
|  |  | 2 | 0 | Negative Control (Blank) Rep 2 |
|  |  | 3 | 0 | Negative Control (Blank) Rep 3 |
|  |  | 4 | Lowest | Lowest Detection Range Calibration Standard Rep 1 |
| 2 | LAL Reagent Water | 5 | Lowest | Lowest Detection Range Calibration Standard Rep 2 |
|  |  | 6 | Lowest | Lowest Detection Range Calibration Standard Rep 3 |
|  |  | 7 | Mid Range | Mid Range Calibration Standard Rep 1 |
|  |  | 8 | Mid Range | Mid Range Calibration Standard Rep 2 |
| 3 | LAL Reagent Water | 9 | Mid Range | Mid Range Calibration Standard Rep 3 |
|  |  | 10 | Highest | Highest Detection Range Calibration Standard Rep 1 |
|  |  | 11 | Highest | Highest Detection Range Calibration Standard Rep 2 |
|  |  | 12 | Highest | Highest Detection Range Calibration Standard Rep 3 |
| 4 | Sample A | 13 | 0 | Sample A Analysis Rep 1 |
|  |  | 14 | 0 | Sample A Analysis Rep 2 |
|  |  | 15 | Mid Range | Positive Control Spike for Sample A Rep 1 |
|  |  | 16 | Mid Range | Positive Control Spike for Sample A Rep 2 |
| 5 | Sample B | 17 | 0 | Sample B Analysis Rep 1 |
|  |  | 18 | 0 | Sample B Analysis Rep 2 |
|  |  | 19 | Mid Range | Positive Control Spike for Sample B Rep 1 |
|  |  | 20 | Mid Range | Positive Control Spike for Sample B Rep 2 |
| 6 | Sample C | 21 | 0 | Sample C Analysis Rep 1 |
|  |  | 22 | 0 | Sample C Analysis Rep 2 |
|  |  | 23 | Mid Range | Positive Control Spike for Sample C Rep 1 |
|  |  | 24 | Mid Range | Positive Control Spike for Sample C Rep 2 |
| 7 | Sample D | 25 | 0 | Sample D Analysis Rep 1 |
|  |  | 26 | 0 | Sample D Analysis Rep 2 |
|  |  | 27 | Mid Range | Positive Control Spike for Sample D Rep 1 |
|  |  | 28 | Mid Range | Positive Control Spike for Sample D Rep 2 |
| 8 | Sample E | 29 | 0 | Sample E Analysis Rep 1 |
|  |  | 30 | 0 | Sample E Analysis Rep 2 |
|  |  | 31 | Mid Range | Positive Control Spike for Sample E Rep 1 |
|  |  | 32 | Mid Range | Positive Control Spike for Sample E Rep 2 |
| 9 | Sample F | 33 | 0 | Sample F Analysis Rep 1 |
|  |  | 34 | 0 | Sample F Analysis Rep 2 |
|  |  | 35 | Mid Range | Positive Control Spike for Sample F Rep 1 |
|  |  | 36 | Mid Range | Positive Control Spike for Sample F Rep 2 |
| 10 | Sample G | 37 | 0 | Sample G Analysis Rep 1 |
|  |  | 38 | 0 | Sample G Analysis Rep 2 |

TABLE 2-continued

| Sample Reservoir | Sample | Optical Chamber | Endotoxin Standard | Description |
|---|---|---|---|---|
| | | 39 | Mid Range | Positive Control Spike for Sample G Rep 1 |
| | | 40 | Mid Range | Positive Control Spike for Sample G Rep 2 |
| 11 | Sample H | 41 | 0 | Sample H Analysis Rep 1 |
| | | 42 | 0 | Sample H Analysis Rep 2 |
| | | 43 | Mid Range | Positive Control Spike for Sample H Rep 1 |
| | | 44 | Mid Range | Positive Control Spike for Sample H Rep 2 |
| 12 | Sample I | 45 | 0 | Sample I Analysis Rep 1 |
| | | 46 | 0 | Sample I Analysis Rep 2 |
| | | 47 | Mid Range | Positive Control Spike for Sample I Rep 1 |
| | | 48 | Mid Range | Positive Control Spike for Sample I Rep 2 |
| 13 | Sample J | 49 | 0 | Sample J Analysis Rep 1 |
| | | 50 | 0 | Sample J Analysis Rep 2 |
| | | 51 | Mid Range | Positive Control Spike for Sample J Rep 1 |
| | | 52 | Mid Range | Positive Control Spike for Sample J Rep 2 |
| 14 | Sample K | 53 | 0 | Sample K Analysis Rep 1 |
| | | 54 | 0 | Sample K Analysis Rep 2 |
| | | 55 | Mid Range | Positive Control Spike for Sample K Rep 1 |
| | | 56 | Mid Range | Positive Control Spike for Sample K Rep 2 |
| 15 | Sample L | 57 | 0 | Sample L Analysis Rep 1 |
| | | 58 | 0 | Sample L Analysis Rep 2 |
| | | 59 | Mid Range | Positive Control Spike for Sample L Rep 1 |
| | | 60 | Mid Range | Positive Control Spike for Sample L Rep 2 |
| 16 | Sample M | 61 | 0 | Sample M Analysis Rep 1 |
| | | 62 | 0 | Sample M Analysis Rep 2 |
| | | 63 | Mid Range | Positive Control Spike for Sample M Rep 1 |
| | | 64 | Mid Range | Positive Control Spike for Sample M Rep 2 |
| 17 | Sample N | 65 | 0 | Sample N Analysis Rep 1 |
| | | 66 | 0 | Sample N Analysis Rep 2 |
| | | 67 | Mid Range | Positive Control Spike for Sample N Rep 1 |
| | | 68 | Mid Range | Positive Control Spike for Sample N Rep 2 |
| 18 | Sample O | 69 | 0 | Sample O Analysis Rep 1 |
| | | 70 | 0 | Sample O Analysis Rep 2 |
| | | 71 | Mid Range | Positive Control Spike for Sample O Rep 1 |
| | | 72 | Mid Range | Positive Control Spike for Sample O Rep 2 |
| 19 | Sample P | 73 | 0 | Sample P Analysis Rep 1 |
| | | 74 | 0 | Sample P Analysis Rep 2 |
| | | 75 | Mid Range | Positive Control Spike for Sample P Rep 1 |
| | | 76 | Mid Range | Positive Control Spike for Sample P Rep 2 |
| 20 | Sample Q | 77 | 0 | Sample Q Analysis Rep 1 |
| | | 78 | 0 | Sample Q Analysis Rep 2 |
| | | 79 | Mid Range | Positive Control Spike for Sample Q Rep 1 |
| | | 80 | Mid Range | Positive Control Spike for Sample Q Rep 2 |
| 21 | Sample R | 81 | 0 | Sample R Analysis Rep 1 |
| | | 82 | 0 | Sample R Analysis Rep 2 |
| | | 83 | Mid Range | Positive Control Spike for Sample R Rep 1 |
| | | 84 | Mid Range | Positive Control Spike for Sample R Rep 2 |
| 22 | Sample S | 85 | 0 | Sample S Analysis Rep 1 |
| | | 86 | 0 | Sample S Analysis Rep 2 |
| | | 87 | Mid Range | Positive Control Spike for Sample S Rep 1 |
| | | 88 | Mid Range | Positive Control Spike for Sample S Rep 2 |
| 23 | Sample T | 89 | 0 | Sample T Analysis Rep 1 |
| | | 90 | 0 | Sample T Analysis Rep 2 |
| | | 91 | Mid Range | Positive Control Spike for Sample T Rep 1 |
| | | 92 | Mid Range | Positive Control Spike for Sample T Rep 2 |
| 24 | Sample U | 93 | 0 | Sample U Analysis Rep 1 |
| | | 94 | 0 | Sample U Analysis Rep 2 |
| | | 95 | Mid Range | Positive Control Spike for Sample U Rep 1 |
| | | 96 | Mid Range | Positive Control Spike for Sample U Rep 2 |

TABLE 3

| Sample Reservoir | Sample | Optical Chamber | Endotoxin Standard | Description |
|---|---|---|---|---|
| 1 | LAL Reagent Water | 1 | 0 | Negative Control (Blank) Rep 1 |
| | | 2 | 0 | Negative Control (Blank) Rep 2 |
| | | 3 | 0 | Negative Control (Blank) Rep 3 |
| | | 4 | Lowest | Lowest Detection Range Calibration Standard Rep 1 |
| | | 5 | Lowest | Lowest Detection Range Calibration Standard Rep 2 |
| | | 6 | Lowest | Lowest Detection Range Calibration Standard Rep 3 |
| | | 7 | Mid Range | Mid Range Calibration Standard Rep 1 |
| | | 8 | Mid Range | Mid Range Calibration Standard Rep 2 |
| | | 9 | Mid Range | Mid Range Calibration Standard Rep 3 |
| | | 10 | Highest | Highest Detection Range Calibration Standard Rep 1 |
| | | 11 | Highest | Highest Detection Range Calibration Standard Rep 2 |

TABLE 3-continued

| Sample Reservoir | Sample | Optical Chamber | Endotoxin Standard | Description |
|---|---|---|---|---|
| | | 12 | Highest | Highest Detection Range Calibration Standard Rep 3 |
| 2 | Sample A | 13 | 0 | Sample A Analysis Rep 1 |
| | | 14 | 0 | Sample A Analysis Rep 2 |
| | | 15 | Mid Range | Positive Control Spike for Sample A Rep 1 |
| | | 16 | Mid Range | Positive Control Spike for Sample A Rep 2 |
| 3 | Sample B | 17 | 0 | Sample B Analysis Rep 1 |
| | | 18 | 0 | Sample B Analysis Rep 2 |
| | | 19 | Mid Range | Positive Control Spike for Sample B Rep 1 |
| | | 20 | Mid Range | Positive Control Spike for Sample B Rep 2 |
| 4 | Sample C | 21 | 0 | Sample C Analysis Rep 1 |
| | | 22 | 0 | Sample C Analysis Rep 2 |
| | | 23 | Mid Range | Positive Control Spike for Sample C Rep 1 |
| | | 24 | Mid Range | Positive Control Spike for Sample C Rep 2 |
| 5 | Sample D | 25 | 0 | Sample D Analysis Rep 1 |
| | | 26 | 0 | Sample D Analysis Rep 2 |
| | | 27 | Mid Range | Positive Control Spike for Sample D Rep 1 |
| | | 28 | Mid Range | Positive Control Spike for Sample D Rep 2 |
| 6 | Sample E | 29 | 0 | Sample E Analysis Rep 1 |
| | | 30 | 0 | Sample E Analysis Rep 2 |
| | | 31 | Mid Range | Positive Control Spike for Sample E Rep 1 |
| | | 32 | Mid Range | Positive Control Spike for Sample E Rep 2 |
| 7 | Sample F | 33 | 0 | Sample F Analysis Rep 1 |
| | | 34 | 0 | Sample F Analysis Rep 2 |
| | | 35 | Mid Range | Positive Control Spike for Sample F Rep 1 |
| | | 36 | Mid Range | Positive Control Spike for Sample F Rep 2 |
| 8 | Sample G | 37 | 0 | Sample G Analysis Rep 1 |
| | | 38 | 0 | Sample G Analysis Rep 2 |
| | | 39 | Mid Range | Positive Control Spike for Sample G Rep 1 |
| | | 40 | Mid Range | Positive Control Spike for Sample G Rep 2 |
| 9 | Sample H | 41 | 0 | Sample H Analysis Rep 1 |
| | | 42 | 0 | Sample H Analysis Rep 2 |
| | | 43 | Mid Range | Positive Control Spike for Sample H Rep 1 |
| | | 44 | Mid Range | Positive Control Spike for Sample H Rep 2 |
| 10 | Sample I | 45 | 0 | Sample I Analysis Rep 1 |
| | | 46 | 0 | Sample I Analysis Rep 2 |
| | | 47 | Mid Range | Positive Control Spike for Sample I Rep 1 |
| | | 48 | Mid Range | Positive Control Spike for Sample I Rep 2 |
| 11 | Sample J | 49 | 0 | Sample J Analysis Rep 1 |
| | | 50 | 0 | Sample J Analysis Rep 2 |
| | | 51 | Mid Range | Positive Control Spike for Sample J Rep 1 |
| | | 52 | Mid Range | Positive Control Spike for Sample J Rep 2 |
| 12 | Sample K | 53 | 0 | Sample K Analysis Rep 1 |
| | | 54 | 0 | Sample K Analysis Rep 2 |
| | | 55 | Mid Range | Positive Control Spike for Sample K Rep 1 |
| | | 56 | Mid Range | Positive Control Spike for Sample K Rep 2 |
| 13 | Sample L | 57 | 0 | Sample L Analysis Rep 1 |
| | | 58 | 0 | Sample L Analysis Rep 2 |
| | | 59 | Mid Range | Positive Control Spike for Sample L Rep 1 |
| | | 60 | Mid Range | Positive Control Spike for Sample L Rep 2 |
| 14 | Sample M | 61 | 0 | Sample M Analysis Rep 1 |
| | | 62 | 0 | Sample M Analysis Rep 2 |
| | | 63 | Mid Range | Positive Control Spike for Sample M Rep 1 |
| | | 64 | Mid Range | Positive Control Spike for Sample M Rep 2 |
| 15 | Sample N | 65 | 0 | Sample N Analysis Rep 1 |
| | | 66 | 0 | Sample N Analysis Rep 2 |
| | | 67 | Mid Range | Positive Control Spike for Sample N Rep 1 |
| | | 68 | Mid Range | Positive Control Spike for Sample N Rep 2 |
| 16 | Sample O | 69 | 0 | Sample O Analysis Rep 1 |
| | | 70 | 0 | Sample O Analysis Rep 2 |
| | | 71 | Mid Range | Positive Control Spike for Sample O Rep 1 |
| | | 72 | Mid Range | Positive Control Spike for Sample O Rep 2 |
| 17 | Sample P | 73 | 0 | Sample P Analysis Rep 1 |
| | | 74 | 0 | Sample P Analysis Rep 2 |
| | | 75 | Mid Range | Positive Control Spike for Sample P Rep 1 |
| | | 76 | Mid Range | Positive Control Spike for Sample P Rep 2 |

TABLE 3-continued

| Sample Reservoir | Sample | Optical Chamber | Endotoxin Standard | Description |
|---|---|---|---|---|
| 18 | Sample Q | 77 | 0 | Sample Q Analysis Rep 1 |
|  |  | 78 | 0 | Sample Q Analysis Rep 2 |
|  |  | 79 | Mid Range | Positive Control Spike for Sample Q Rep 1 |
|  |  | 80 | Mid Range | Positive Control Spike for Sample Q Rep 2 |
| 19 | Sample R | 81 | 0 | Sample R Analysis Rep 1 |
|  |  | 82 | 0 | Sample R Analysis Rep 2 |
|  |  | 83 | Mid Range | Positive Control Spike for Sample R Rep 1 |
|  |  | 84 | Mid Range | Positive Control Spike for Sample R Rep 2 |
| 20 | Sample S | 85 | 0 | Sample S Analysis Rep 1 |
|  |  | 86 | 0 | Sample S Analysis Rep 2 |
|  |  | 87 | Mid Range | Positive Control Spike for Sample S Rep 1 |
|  |  | 88 | Mid Range | Positive Control Spike for Sample S Rep 2 |
| 21 | Sample T | 89 | 0 | Sample T Analysis Rep 1 |
|  |  | 90 | 0 | Sample T Analysis Rep 2 |
|  |  | 91 | Mid Range | Positive Control Spike for Sample T Rep 1 |
|  |  | 92 | Mid Range | Positive Control Spike for Sample T Rep 2 |
| 22 | Sample U | 93 | 0 | Sample U Analysis Rep 1 |
|  |  | 94 | 0 | Sample U Analysis Rep 2 |
|  |  | 95 | Mid Range | Positive Control Spike for Sample U Rep 1 |
|  |  | 96 | Mid Range | Positive Control Spike for Sample U Rep 2 |

During the testing process of disc 103 within reader 100, when the fluid is positioned within the optical chamber 202 for optical analysis, the reader 100 is configured to conduct optical testing, such as optical spectrometry, recording the data analyzed, and compile the recorded data.

The disc 103 and reader 100 provide faster analysis time compared to standard microplate methods for testing for bacterial endotoxins as well as any other fluid testing. The disc 103 requires much less preparation time than typical microplates, resulting in less chance of contamination, easier to integrate into other laboratory tasks, and lower costs. The disc 103 and reader 100 meet all the valid test requirements of USP <85> Bacterial Endotoxin Test for turbidimetric or chromogenic techniques, including preparatory testing which includes assurance of criteria for the calibration curve and test for interfering factors. This includes verifying the test procedure, calculation, interpretation, and results, in the case of LAL Reagent Water, are less than 0.25 EU/ml and in the case of product the endotoxin is less than the limit for the product. Each fluid sample, blank, and calibration endotoxin test is internally validated within reader 100, which includes means to validate the tests including, but not limited to, sample critical optical quality blank reading, mixed sample/reagents/optional endotoxin, initial optical reading, smoothness of the change and rate of change of the critical optical quality, closeness of fit to theoretical expected change, expectations on the noise level of the data, and the like. If test results appear incorrect the testing process for a disc 103 will be stopped and an error message will be sent to user interface 113 and/or input device 114 without producing an endotoxin measurement result. There is no attachment of reagents onto optical windows 205 to allow the initial critical optical quality measurement of the fluid sample prior to the addition or mixing of reagents with the fluid.

"Validate" as used herein means to substantiate, confirm the quality of, or establish the certainty of the analysis or progress of the analysis. When validating the suitability of the analysis, compendia methods may be used wherein at least two positive controls (samples spiked with LAL-reactive substances at the middle of the calibration range), three negative controls (blanks), and any other parameters specified by the manufacturer or compendia are required. The positive product control spikes must meet compendia requirements (between 50% and 200% spike yield), the negative control (difference between lowest level and blank, with the blank having a lower response level), and the manufacturers specification (e.g. the difference between a 0.005 EU/mL sample and blank, or onset time limits for certain standards). If these analyses are successful, they validate that the system and reagents are operating to specification. To validate the data stream means that the data streams' behavior statistically corresponds to the expected behavior based on historical measurement data or the known reaction kinetics of the reaction between the detection reagent and LAL-reactive substance. This shows that the data stream is being generated by a change in the analysis chamber based on the LAL reaction and not a change in the chamber or optical path based on some abnormality, such as a bubble. Ultimately this differentiation would itself be validated by multiple tests on different reagents and lots and induced anomalies to confirm its operation, including, but not limited to, sample critical optical quality blank reading, mixed sample/reagents/optional LAL-reactive substances, initial optical reading, smoothness of the change and rate of change of the critical optical quality, closeness of fit to theoretical expected change, expectations on the noise level of the data, and the like. If test results appear incorrect the testing process for a module will be stopped and an error message will be sent without producing an LAL-reactive substances measurement result.

Reader 100 and disc 103 are configured to prevent introduction errors by the fluid sample. In an embodiment, reader 100 and/or disc 103 includes visual feedback for placement of fluid samples, which may include colored or marked fields or other active optical feedback. Reader 100 and disc 103 are also configured to minimize pipetting errors.

Each fluid sample is automatically aliquoted for multiple testing. Each fluid sample is injected in one reservoir 325 (in an embodiment about 100 μl of fluid) and split into 4 equal aliquots of fluid to meet the requirements of USP <85> Bacterial Endotoxin Test standard. The user only injects fluid samples and LAL Reagent Water into disc 103. Because of the reduced amount of fluid sample used for testing, a similarly less amount of reagent is required for a testing process, and a reduced amount of necessary reagent results in a cheaper test for bacterial endotoxin.

The reader 100 and disc 103 are also configured to predict BET measurement results. The reader 100 and disc 103 include means to accurately predict the concentration of endotoxin in the samples by monitoring the critical optical quality (transmission, absorption, optical density, color, color value, hue, spectrum, turbidity, scattered light, chemiluminescence, or florescence) as a function of time and applying various prediction algorithms. The prediction is used to speed up measurement time to final results. The reader 100 and disc 103 also allow for signal extraction from noise during the optical analysis. The reader 100 and disc 103 also provides for the use of the kinetic reaction model or other reaction models. Disc 103 includes optional active fluid sample degassing using hydrophobic membranes and multiple sample movement past the membrane or degassing while sample is not moving and is in static contact with the membrane.

Reader 100 and disc 103 include ways to indicate which reservoir 325 is to be filled by the user with an option to associate an entered label or identifier for the sample into reader 100, automatic analysis of results including calculations, automatic report of all results required by the user and regulatory requirements. Reader 100 also allows for generation of reports that to include all relevant information on disc 103, reagent age, and shelf life limits.

Reagents—including LAL, endotoxin, and optional chromogenic reagent, and the like—can be preloaded at the correct levels in disc 103 by any practical means including immobilization of the reagents onto the walls of optical chamber 202, addition of dissolvable reagents in various forms (beads), or attached to dissolvable and non-dissolvable films or forms inserted into disc 103. Disc 103 and reader 100 are configured to reduce or eliminate contamination. Disc 103 includes a sealing means to block the transmission of water, oxygen, endotoxin, and bacteria into and through disc 103.

Reader 100 can include a heater or other apparatus to heat disc 103 to a controlled temperature, and, in an embodiment, prior to introduction of the fluid samples. Heater of reader 100 can be located in spindle 104, sometimes called a mandrel. Some embodiments of reader 100 heat disc 103 via air-based thermal transfer using a sheer layer next to rotating disc 103, which is rapid and uniform, lower cost, and east to control or regulate. It is contemplated that some embodiments of reader 100 preheat disc 103 by heating the interior of the enclosure or the mandrel. Reader 100 can be configured to measure the optical density of the samples in disc 103 before, during, and at the end of the reaction.

Disc 103, as explained above, can include reagents, such as, for example, LAL, endotoxin, and/or chromogenic reagents. The reagents are stabilized for long shelf life with addition of additives using slow or rapid drying methods. The reagents/reactants can be configured to control solvation rate when reconstituted with the fluid sample. Both slow drying and rapid lyophilization can be used, based on proven ability to re-dissolve without loss of sensitivity for the endotoxin measurement. Extraction of pyrogenic natural materials from bacteria can be used to create material that solubilizes quickly, prevents bio-molecular aggregates, and has good stability. These extracts can be Control Standard Endotoxins, CSE, sourced from licensed LAL manufacturers to match LAL reagent lots, or Reference Standard Endotoxin, RSE, which is universal and does not need to be matched to lots. The use of RSE allows the manufacture of devices which can be used with any LAL reagent, an advantage in manufacturing and distribution because variants with specific reagents are unnecessary. The reagents are deposited in disc 103 to control deposition accuracy, isolation of different reagent components to prevent premature interaction, and optimized mixing from best physical arrangement. The reagents are designed for fast solvation to increase accuracy of optical measurement. The rate of solvation should be controlled so that the mixing with the fluid sample has maximum efficiency. Solvation of the reagents can be controlled so that optical analyses can start at known or pre-determined times, which increasing accuracy of the optical measurement.

Bubbles can interfere with motion of the fluid and the optical properties of the fluid, and their control is important to a robust analytical system. Further, bubbles can be controlled in disc 103 using centripetal force, such as during readings with disc spinning Normally, bubbles do not separate well at normal gravitational force due to their small size and ability to stick to surfaces. However, the centripetal force of a spinning disc can exceed the normal gravitational force as the rotational velocity of the disc increases, thereby naturally eliminating bubbles. This allows for multiple methods or reagent or standard immobilization that might generate bubbles.

Reader 100 and disc 103 improves the measurement of bacterial endotoxins within a fluid sample by improving the test accuracy, decreasing errors in measurement (timing, thermal variations, reaction initiation, reagent mixing, and optical measurements), decreasing sample contamination, increasing sample through-put, decreasing total test time, utilizing built-in test validations to increase reliability, and meeting all global regulatory agency and pharmacopeia requirements. The test for bacterial endotoxins is semi-automated using reader 100 and disc 103 which allow a high density of tests to be accomplished with a minimum amount of user input.

In one embodiment, standard is a control standard endotoxin extracted from pyrogenic natural material for use as an analyte reference to have optimum physical characteristics for use with disc 103 and reader 100, such as optimum solvation rates, micelle formation (bio-molecular aggregates), and stability.

It is contemplated that in some embodiments of disc 103, multiple reagents can be immobilized in optical chamber 202. In these embodiments, the reagents are accurately placed on optical chamber 202 such that the reagents are isolated from one another and physically arranged for controlled mixing, such that the reagents do not interact prematurely.

As can be seen, since reader 100 and disc 103 reduce the amount of preparation time and reduce the likelihood of contamination, this allows disc 103 and reader 100 to be integrated easier into the lab, reduce the cost of reader 100 and disc 103, provide for a faster analysis time, reduce technician training time, increase robustness of testing quality, and reduce the amount of time technicians require to carry out the tests. The faster analysis time is due to shorter preparation time and extrapolation of an endpoint.

Further, since disc 103 is contained inside of enclosure 101 of reader 100 and the fluidics network 600 of disc 103 is largely sealed, there is less chance of contaminants entering disc 103 and interfering with testing. Such contaminants may include, endotoxins, glucans, biochemicals, enzyme inhibiting ions, and optical contaminants (e.g. fingerprints on surfaces, such as optical windows 205). This is due to the fact that there is better control of the testing environment inside enclosure 101 and disc 103 requires less handling during testing. Further, due to the control of the environment within enclosure 101 and the form and volume of disc 103, enclosure 101 and disc 103 give faster and better thermal control and material control, such as through reduced contamination and toxicity of component surfaces.

Further, the microfluidic properties of disc 103 provide for one or both of active mixing and passive mixing of the fluid therewithin during testing. Active mixing may be comprised of one or more of stirring using inertial force, the Coriolis effect to spin the sample, various channels, networks, or chambers that effect mixing as fluids are resident or pass through them, either in one direction or reciprocally, or mechanical or acoustic actuators that physically stir the sample. Passive mixing may comprise methods utilizing diffusion in narrow chambers of disc 103.

The design of the fluidics network 600 of disc 103 uses a lower volume of reagents, which leads to a lower material cost for running a test, lower input on natural resources, and less waste.

As can be seen in disc 103 and reader 100, in accordance with the compendia methods, licensed reagents are used, each sample is assayed in duplicate, and each sample is assayed with a positive control spike at the middle level in duplicate. Further, calibration is performed in triplicate at low, middle, and high levels, wherein decade (10. times.) changes in concentration give a wide range, and compendia (e.g. USP 85) requires triplicate replications when it's the first time a new lot of reagent is used, so by always doing triplicate replication we cover every case. Negative controls are also performed in triplicate in accordance with the same logic for performing calibration in triplicate. It is contemplated that some embodiments of disc 103 only have duplicate calibration and negative control replication because that is all that is required for subsequent uses of a reagent lot under compendia. Where non-compendia methods are acceptable or have been validated as being equivalent and acceptable to regulatory agencies, a stored calibration based on historical data can be used instead of the results from individual standards.

Further, as can be seen in disc 103, since precise volumes of sample fluid and reagent are needed during aliquoting and distribution, a single sample can be split into four or more analysis with duplicate replications on assay with and without positive control spike, and LAL Reagent Water used as sample for calibration and negative controls could be split into four assays to use identical fluidics testing areas. Further, positive control spikes and calibration standards can be mixed into samples during aliquoting or distribution. Additionally, excess sample can be drained off and stored in disc 103, which makes transfer of samples easier because they do not have to be an exact volume.

Further, as can be seen, disc 103 is configured to receive twenty-one (21) samples of fluid to be tested, in addition to a blank test as well as establishing a calibration curve, as provided in the BET. It should be understood by one of ordinary skill in the art that although the exemplary disc 103 shown and described herein includes twenty-four (24) radial testing areas 303 formed therein, other embodiments of disc 103 can be formed with more or fewer radial testing areas 303. It should also be understood by one of ordinary skill in the art that although the discussion herein is in reference to the use of disc 103 for carrying out the testing array provided in the BET, disc 103 can also be configured to be used in any other testing method for testing fluid samples and providing a calibration test as well as a baseline test.

While this invention has been described in conjunction with the specific embodiments described above, it is evident that many alternatives, combinations, modifications and variations are apparent to those skilled in the art. Accordingly, the embodiments of this invention, as set forth above are intended to be illustrative only, and not in a limiting sense. Various changes can be made without departing from the spirit and scope of this invention. Therefore, the scope of the present invention is defined by the appended claims, and all devices, processes, and methods that come within the meaning of the claims, either literally or by equivalence, are intended to be embraced therein.

The invention claimed is:

1. A reader configured to test fluid samples in a microfluidic disc, said reader comprising: an enclosure, an optical bench, a centripetal disc drive, and a controller; wherein said microfluidic disc comprises at least two testing areas; wherein each testing area includes:
   a reservoir portion for receiving at least one fluid sample, said reservoir portion comprising a reservoir and a reservoir outlet;
   and a distribution network portion in fluid communication with said reservoir portion;
   wherein each distribution network portion comprises a distribution network of at least four (4) testing channels, wherein each testing channel has a metering portion and at least one analysis chamber portion, said metering portion being sized to meter an aliquot of said fluid sample for analysis in said analysis chamber portion;
   wherein said distribution network portion further comprises a main distribution channel in fluid communication with said reservoir outlet, said metering portions are in fluid communication with said main distribution channel, a waste inlet channel in fluid communication with said main distribution channel, and a waste chamber in fluid communication with said waste inlet channel for confining any excess of said fluid sample and separating said excess fluid sample from said aliquot;
   said microfluidic disc being removably securable to said centripetal disc drive within said enclosure, such that a measurement of changes in said at least one fluid sample may be taken, when each of said testing areas rotates through said optical bench; wherein said rotation and said measurement are controlled by said controller.

2. The reader of claim 1, wherein said enclosure includes an inlet for inserting a fluid sample into a reservoir of said disc, wherein said inlet and reader are configured to prevent the user from inserting said fluid sample into an incorrect reservoir.

3. The reader of claim 1, wherein at least one distribution network is a calibration network comprising at least eight (8) testing channels and wherein:
   at least two (2) of said channels have no Limulus Amebocyte Lysate ("LAL") reactive substance therein;
   at least two (2) of said channels have a first amount of a LAL-reactive substance isolated therein;
   at least two (2) of said channels have a second amount of a LAL-reactive substance isolated therein; and at least two (2) of said channels have a third amount of a LAL-reactive substance isolated therein.

4. The reader of claim 1, wherein at least one distribution network is a sample measurement network comprising at least four (4) testing channels and wherein:
   at least two (2) of said channels have no LAL-reactive substance therein;
   at least two (2) of said channels have a spike with a fourth amount of a LAL-reactive substance isolated therein.

5. The reader of claim 1, wherein at least one valve is positioned between a) said reservoir portion and said distribution network portion, and/or b) said metering portion and said analysis chamber portion.

6. The reader of claim 5, wherein said valve is configured to allow centrifugal forces to motivate said aliquot to flow across said valve from said metering portion to said analysis chamber portion.

7. The reader of claim 1, wherein all of said analysis chamber portions comprise a mixing chamber and an optical chamber, said mixing chamber having at least one additional reagent isolated therein, said additional reagent comprising a detection reagent.

8. The reader of claim 7, wherein said mixing chamber has thick sidewalls optimized for mixing said detection reagent immobilized on said sidewalls with said aliquot, wherein said thick sidewalls promote flow paths that mix said reagents and said aliquot close to said thick sidewalls.

9. The reader of claim 1, wherein said analysis chamber is configured to enable mixing said aliquot with said reagent using at least one of the Coriolis effect, inertial effect, or bubbles and/or beads entrained therein.

10. The reader of claim 1, wherein said disc is configured to allow centrifugal forces to eliminate bubbles from said sample fluid in said optical chamber portion.

\* \* \* \* \*